(12) United States Patent
Buchholz et al.

(10) Patent No.: US 6,673,336 B2
(45) Date of Patent: *Jan. 6, 2004

(54) CONJUGATE, ITS PREPARATION AND USE

(75) Inventors: Herwig Buchholz, Frankfurt am Main, DE (US); Eike Poetsch, Mühltal, DE (US); Ralf Rosskopf, Münster, DE (US); Ralf Anselmann, Ramsen, DE (US); Michael Kirschbaum, Weiterstadt, DE (US); Frank Pflücker, Darmstadt, DE (US)

(73) Assignee: Merck Patent, GmbH (DE)

( * ) Notice: Subject to any disclaimer, the term of this patent is extended or adjusted under 35 U.S.C. 154(b) by 50 days.

This patent is subject to a terminal disclaimer.

(21) Appl. No.: 10/010,449

(22) Filed: Nov. 7, 2001

(65) Prior Publication Data

US 2002/0160027 A1 Oct. 31, 2002

(30) Foreign Application Priority Data

Nov. 9, 2000 (DE) .......................... 100 55 588

(51) Int. Cl.[7] .............................. A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS

| | | | | |
|---|---|---|---|---|
| 5,252,323 A | * | 10/1993 | Richard et al. | 424/59 |
| 5,601,811 A | * | 2/1997 | Gallagher et al. | 424/709 |
| 5,882,632 A | * | 3/1999 | Allard et al. | 424/59 |

* cited by examiner

*Primary Examiner*—Shelley A. Dodson
(74) *Attorney, Agent, or Firm*—Jenkins, Wilson & Taylor, P.A.

(57) ABSTRACT

The invention relates to a conjugate which can be used for preparing dermatological and cosmetic compositions. The invention also relates to processes for preparing such conjugate and to its use.

33 Claims, No Drawings

CONJUGATE, ITS PREPARATION AND USE

DESCRIPTION

1. Technical Field

The present invention relates to a conjugate, which can be used for the preparation of dermatological and cosmetic compositions. The invention also relates to processes for preparing such conjugate and to its use.

2. Related Art

Dermatological or cosmetic compositions are used for example to protect the skin against harmful external effects, such as against sun radiation. In modern society a more or less marked tanning of skin is considered to be attractive and an expression of dynamics and sportiveness. Besides this desired effect of sun on skin also a series of undesired side effects is occurring such as sunburn or premature aging of skin and wrinkling. Meanwhile a number of efficient UV filters has been developed which, applied onto the skin in the form of creams, lotions or gels can inhibit effectively the development of sunburn even under a more intensive exposure to sun. The UV filters contained in the pharmaceutical or cosmetic preparations form a film and a layer, respectively, on the surface of the skin. The known UV filters and sun protecting agents act in such manner that they absorb certain parts of sunlight so that this radiation cannot penetrate into deeper layers of the skin. It is known that the most dangerous part of the sun radiation is formed by the ultraviolet rays having a wavelength of less than 400 nm. The lower limit of the ultraviolet rays which reach the surface of earth by the absorption in the ozone layer is restricted to about 280 nm. The sun filter commonly used in the cosmetics absorb in a wavelength range of from 280 to 400 nm. This range comprises UVB rays having a wavelength between 280 and 320 nm which play a decisive roll in the formation of a sun erythema, as well as UVA rays having a wavelength between 320 and 400 nm which cause tanning but also aging of skin, promote the initiation of an erythematic reaction or increase this reaction with certain individuals or even may initiate phototoxic or photoallergic and irritative reactions.

Light protection formulations which have been applied onto the skin have the purpose to hold back skin damaging parts of radiation. As light filters inorganic or organic materials can be used.

Light protection formulations based on organic light filters contain organic light filters which are soluble in water and/or oil or are soluble neither in water nor in oil.

Light protection formulations having insoluble particulate organic light filters are described for example in WO 97/3643. The group of insoluble organic light filters is, however, restricted to a few classes of compounds.

Light protection formulations having organic light filters and being soluble in water and/or oil are described in publications DE-A-197 46 654, DE-A-197 55 504, EP-A-709 080, EP-A-775 698, EP-A-893 119 and U.S. Pat. No. 5,882,632.

In DE-A-197 46 654 the use of 4,4-diaryl-butadiene derivatives as soluble organic light filter in light protection formulations for protecting skin against UVA radiation is described.

The above mentioned light protection formulations must contain the organic light filters in a high concentration in order to ensure a sufficient light protection. However, the most serious disadvantage of organic soluble light filters consists in that optionally they penetrate into the skin due to their solubility and can cause skin damages or allergies.

In JP-A-11-255 630 a light protection formulation for protecting the skin against UVA radiation is described which contains a dibenzoyl methane derivative and is applied to a silicone polymer-coated inorganic support. However, the preparation of this light protection formulation is troublesome and time consuming due to a multitude of operations. Furthermore, dibenzoyl methane derivatives are not photostable (light-resistant).

Dermatological and cosmetic compositions can further contain a multitude of active substances, such as organic substances having antioxidative and/or radical inhibiting properties as well as repellants.

In general, a heterogenisation of the active substances contained in dermatological and cosmetic compositions is desirable, since i.a. a penetration into the skin and a possibly resulting skin damage or allergy can be prevented.

SUMMARY OF THE INVENTION

It is an object of the present invention to provide a conjugate based on organic active substances and which cannot penetrate into the skin.

This object is achieved according to the present invention by providing a conjugate which comprises an inorganic pigment and an active substance based on organic compounds, the active substance being covalently bound through a spacer group to the inorganic pigment. The conjugate of the invention is characterized in that the spacer group contains an element of the groups 3A, 4A, 3B, 4B, 5B and 6B of the periodic table of elements.

The invention also provides a dermatological or cosmetic composition comprising at least one conjugate of the above mentioned type and at least one cosmetically, pharmaceutically and/or dermatologically compatible vehicle and/or adjuvant.

In the frame of the present invention the expression "conjugate" means a product which is obtained by a molecular i.e. covalent bond between the active substance and the inorganic pigment. The expression "active substance" comprises for example light absorbing organic compounds, substances having antioxidative and/or radical inhibiting properties, repellants, preservatives and derivatives of these active substances which can be bound covalently through a spacer group to an inorganic pigment. The active substance or derivative thereof comprises preferably a nucleophilic group. It is preferred that the active substance per se, i.e. without being bound to an inorganic pigment, is water soluble and/or oil soluble.

The conjugate of the invention contains an inorganic pigment. In the frame of the present invention the expression "pigment" means a dye (colorant) or filler being insoluble in the application medium. The inorganic pigment in the conjugate of the invention preferably is a metal oxide or a semi-metal oxide.

Examples of inorganic pigments comprise oxides, silicates, phosphates, carbonates, sulfates and nitrides, oxides being preferably used.

Preferred inorganic pigments comprise magnesium oxide, aluminum oxide, silicon dioxide, zinc oxide, cerium oxide, titanium dioxide, zirconium oxide, manganese oxide, boron oxide, red or black iron oxide, talc, kaolin, natural and synthetic mica materials, such as muscovite, phlogopite, lepidolite, biotite and vermiculite, magnesium carbonate, calcium carbonate, aluminum silicate, barium silicate, calcium silicate, magnesium silicate, strontium silicate, barium sulfate, calcium sulfate, calcium phosphate, fluoroapatite, hydroxyapatite, ceramic powder, boron nitride, iron titanate, zeolite and mixtures thereof. Silicon dioxide, titanium dioxide, mica, talc and mixtures of the above mentioned pigments (in the following called "mixed pigments") such as silicon dioxide/titanium dioxide are particularly preferably used.

Commercially available inorganic mixed pigments which can be used according to the invention comprise mixtures of titanium dioxide/mica, titanium dioxide/mica/tin oxide, titanium dioxide/mica/iron oxides, titanium dioxide/mica/silicon dioxide, titanium dioxide/mica/carmine, mica/iron oxides/aluminum oxide, mica/iron oxides, titanium dioxide/mica/zinc oxide, titanium dioxide/mica/barium sulfate, mica/silicon dioxide and titanium dioxide/iron oxides/silicon dioxide. These mixed pigments are sold under the names Timiron®, Soloron®, Colorona®, Dichrona®, Microna®, Micronaspher® and Ronaspher®.

Light scattering pigments such as Ronaspher® LDP as well as nacreous pigments can also be used.

The silicates can have a chain, belt or sheet-shaped structure. Silicates having a sheet-shaped structure such as mica or talc are preferably used.

The form in which the metal oder semi-metal compound is present, is not restricted to certain forms.

The metal or semi-metal compound has preferably the form of spherical particles. Suitable materials based on silicon dioxide comprise commercially available products offered under the name Monospher®, such as Monospher® 10(silicon dioxide having a particle size of 10 nm), Monospher® 25(silicon dioxide having a particle size of 25 dioxide having a particle sire of 100 nm) or Monospher® 500 (silicon dioxide having a particle size of 500 nm), or Ronaspher® (silicon dioxide having a particle size of from 50 nm to 3 $\mu$m).

The preparation of monodisperse spherical oxide particles is known. According to the process described in EP-A-216 278 monodisperse spherical oxide particles can be obtained by hydrolytic polycondensation of alkoxides.

Other preferred forms in which the metal or semi-metal compounds can be present comprise needles and flocs.

DETAILED DESCRIPTION OF THE INVENTION

The active substances based on organic compounds which according to the invention are bound covalently to an inorganic pigment comprise for example light absorbing organic compounds, substances having antioxidative and/or radical inhibiting properties, repellants as well as preservatives. However, the active substances used according to the invention are not limited to these active substances.

The light absorbing organic compounds are selected from compounds which absorb UV light. Compounds are used which absorb UV light in the UVB range, i.e. in the range of from 280 to 320 nm and/or in the UVA range, i.e. in the range of from 320 to 400 nm.

UVB filters preferably exhibit a maximum of absorption in the range of from 300 to 320 nm and they can be selected from known substandes already described in the literature. Examples comprise derivatives of aminobenzoic acid, cinnamic acid, salicylic acid, benzylidene camphor, phenyl benzimidazole, diphenylacrylate, triazine, triazole and vinyl group-containing amides.

Examples of aminobenzoic acid derivatives comprise 4-aminobenzoic acid, 4-aminobenzoic acid-2,3-dihydroxypropyl ester, 4-[bis(2-hydroxypropyl)-amino] benzoic acid ethylester, 4-(dimethylamino)benzoic acid-2-ethylhexylester (e.g. Eusolex® 6007) and ethoxylated 4-aminobenzoic acid ethylester (e.g. Uvinul® P25).

Examples of cinnamic add derivatives comprise cinnamic acid esters like p-methoxy-cinnamic acid-2-ethylhexylester (e.g. Eusolex® 2292), 4-methoxy-cinnamic acid isopentylester, e.g. in the form of a mixture of the isomers (e.g. Neo Heliopan® E 1000) and 4-methoxy-cinnamic acid-2-methylhexylester, as well as the diethanolamine salt of 4-methoxy-cinnamic acid and cinnamic acid derivatives as described in U.S. Pat. No. 5,601,811 and in WO 97/851.

The salicylic acid derivatives include for example 2-ethylhexyl salicylate (e.g. Eusolex® OS), 4-isopropyl-benzylsalicylate (e.g. Megasol®) and 3,3,5-trimethylcyclohexyl-salicylate (e.g. Eusolex® HMS).

Examples for benzylidene camphor derivatives comprise 3-(4'-methyl-benzylidene)di-camphor (e.g. Eusolex® 6300), 3-benzylidene camphor (e.g. Mexoryl® SD), polymers of N-{(2- and 4)-[(2-oxoborn-3-ylidene)methyl]-benzyl)-acrylamide (e.g. Mexoryl® SW), N,N,N-trimethyl-4-(2-oxoborn-3-ylidenemethyl)anilinium methylsulfate (e.g. Mexoryl® SK) and α-($^2$oxoborn-3-ylidene)toluene-4-sulfonic acid (e.g. Mexoryl® SL).

As examples of phenylbenzimidazole derivatives 2-phenylbenzimidazole-5-sulfonic acid and its potassium, sodium and triethanolamine salts can be mentioned (e.g. Eusolex® 232).

Special examples of diphenylacrylate derivatives comprise 2-cyano-3,3'-diphenylacrylic acid-2-ethylhexylester and 2-cyano-3,3'-diphenylacrylic acid ethylester.

Examples of triazole derivatives comprise benzotriazoles, such as 2-(2-hydroxy-5-methylphenyl)benzotriazole as well as the triazoles described in EP-A-893 119.

Special examples of triazines comprise 2,4,6-tri-{-4-[(2-ethylhexyl)oxycarbonyl]-phenylamino}-1,3,5-triazine as well as the compounds described in EP-A893 119. Further examples comprise trianiline-triazine derivatives as disclosed in U.S. Pat. No. 5,332,568, EP-A-570 838, EP-A-517 104, U.S. Pat. No. 5,252,323, WO 93/17002 and WO 97/03642, hydroxyphenyltriazine derivatives as described in EP-A-775 698 as well as bis-resorcinol-dialkylaminotriazines as disclosed for example in EP-A-780 382.

Preferred examples of vinyl group-containing amide derivatives comprise those described in EP-A-893 119.

As UVA filter substances preferably compounds can be used which exhibit a maximum of absorption in the range of from 330 to 380 nm. Any known UVA filter substances like derivatives of benzophenone, dibenzoylmethane, diarylbutadiene and triazine can be used.

Special examples of benzophenone derivatives comprise 2-hydroxy-4-methoxybenzophenone (e.g. Eusolex® 4360), 2-hydroxy-4-methoxybenzophenone-5-sulfonic acid and its sodium salt (e.g. Uvinul® MS-40), as well as 8-(2,2'-di-hyrohydroxy-4methoxybenzophenone).

Special examples of benzoylmethane derivatives and dibenzoylmethane derivatives comprise 1-(4-tert-butylphenyl)3-(4-methoxyphenyl)-propane-1,3-dione (e.g. Eusolex® 9020) and 4-isopropyldibenzoylmethane (e.g. Eusolex® 8020).

Examples of diarylbutadiene derivatives comprise the 4,4-diarylbutadienes described in DE-A-197 46 654, in particular 4,4-diphenylbutadiene.

Special examples of triazines comprise 2,4-bis-{[4-(2-ethylhexyloxy)-2-hydroxy]-phenyl}-6-(4-methoxyphenyl)-1,3,5-triazine.

Further suitable UV filters comprise 2-cyano-3,3-diphenylacrylic acid-2-ethylhexylester (e.g. Eusolex® OCR), 3,3'-(1,4-phenylenedimethylene)-bis-(7,7-dimethyl-2-oxobicyclo-[2.2.1]hept-1-ylmethanesulfonic acid and its salts (e.g. Mexoryl® SX), 2,4,6-trianilino(p-carbo-2'-etylhexyl-1'-oxy)-1,3,5-triazine (e.g. Uvinul® T 150), 2-(2H-benzotriazole-2-yl)-4-methyl-6-(2-methyl-3-(1,3,3,3-tetramethyl-1-(trimethylsilyloxy)disiloxanyl)propyl)-phenol (e.g. Silatrizole®), 4,4'-[(6-[4-((1,1-dimethyl-ethyl)aminocarbonyl)phenylamino]-1,3,5-triazine-2,4-diyl)diimino]bis(benzoic acid-2-ethylhexylester) (e.g. Uvasorb® HEB), α-(trimethylsilyl)-ω-[trimethylsilyl)oxy]poly[oxy-(dimethyl [and about 6% methyl[2-[p-[2,2-bis (ethoxycarbonyl]vinyl]phenoxy]-1-methylene-ethyl] and ca. 1.5% methyl[3-[p-[2,2-bis(ethoxycarbonyl)vinyl] phenoxy)-propenyl) and 0.1 to 0.4% (methylhydrogen] silylene]] (n≈60) (CAS-No. 207 574-74-1), 2,2'-methylene-bis-(6-(2H-benzotriazole-2-yl)-4-(1,1,3,3-tetramethylbutyl) phenol) (CAS-No. 103 597-45-1), 2,2'-(1,4-phenylene)bis-(1H-benzimidazole-4,6-disulfonic acid, monosodium salt) (CAS-No. 180 898-37-7) and 2,4-bis-{[4-(2-ethyl-hexyloxy)-2-hydroxyl]-phenyl}-6-(4-methoxy-phenyl)-1,3,5-triazine (CAS-No. 103 597-45-, 187 393-00-6).

Preferred UV radiation absorbing organic compounds are 3-(4'-methyl-benzylidene)-dl-camphor, 1-(4-tert-butylphenyl)-3-(4-methoxyphenyl)-propane-1,3-dione, 4-isopropyl-dibenzoylmethane, 2-hydroxy-4-methoxy-benzophenone, methoxycinnamic acid octylester, methoxycinnamic acid octylester, 3,3,5-trimethylcyclohexyl-salicylate, 4-(dimethylamino)-benzoic acid-2-ethylhexylester, 2-cyano-3,3-diphenylacrylic acid-2-ethylhexylester, 2-phenylbenzimidazole-5-sulfonic acid as well as its potassium, sodium and triethanolamine salts.

Photostable UV radiation absorbing organic compounds are preferably used, photostable UVA filters and UVB filters being particularly preferably used.

Suitable substances having antioxidative and/or radical inhibiting properties comprise for example flavonoides, coumaranones, amino acids (e.g. glycine, histidine, tyrosine, tryptophane) and derivatives thereof, imidazoles, (e.g. uro-caninic acid) and derivatives thereof, peptides such as D,L-carnosine, D-carnosine, L-carnosine and derivatives thereof (e.g. anserine), carotinoides, carotines (e.g. α-carotine, β-carotine, lycopine) and derivatives thereof, chlorogenic acid and derivatives thereof, liponic acid and derivatives thereof (e.g. dihydroliponic acid), aurothioglucose, propylthiouracile and other thioles (e.g. thioredoxine, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof, diaurylthiodipropionate, distearylthiodipropionate, thio-dipropionic acid and derivatives thereof (esters, ethers, peptides, lipides, nucleotides and nucleosides) as well as sulfoximine compounds (e.g. buthionine sulfoximines, homocysteine sulfoximine, buthionine sulfones, penta, hexa, heptathionine sulfoximine), chelating agents (e.g. α-hydroxy fatty acids, paimitic acid, phytinic acid, lactoferrin), α-hydroxy acids (e.g. citric acid, lactic acid, malic acid), huminic acid, gallic acid, gall extracts, bilirubin, biliverdin, EDTA, EGTA and derivatives thereof, unsaturated fatty acids and derivatives thereof, vitamin C and derivatives (e.g. ascorbyl palmitate, ascorbyl acetate), tocopheroles and derivatives (e.g. vitamin E acetate), vitamin A and derivatives (e.g. viamin A palmitate) as well as coniferyl benzoate of benzoic resin, rutinic acid and derivatives thereof, α-glycosylrutin, ferula acid, furfurylidene glucitol, carnosine, butylhydroxytoluene, butylhydroxyanisol, nor-dohydroguajaretic acid, trihydroxybutyrophenone, quercitin, ureic acid and derivatives thereof, mannose and derivatives thereof, vitamin E and derivatives thereof, stilbenes and derivatives thereof (e.g. stilbene oxide, trans-stilbene oxide) as well as BHT (2,6-di-tert-butyl-4-methylphenol).

Preferred antioxidants comprise flavonoides, coumaranones, vitamins and BHT.

The glucosides of flavanones, flavones, 3-hydroxyflavones (=flavanoles), aurones, isoflavones and rotenoides are considered as flavanoides (Römpp Chermie Lexikon, Vol. 9, 1993). However, in the frame of the present invention they also comprise the aglycones, i.e. the sugar-free components and the derivatives of flavonoides and aglycones. In the frame of the present invention the coumaranones also comprise their derivatives.

Preferred flavonoides are derived from flavanones, flavones, 3-hydroxyflavones, aurones and isoflavones, in particular from flavanones, flavones, 3-hydroxyflavones and aurones.

The flavanones are characterized by the following basic structure:

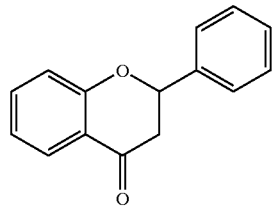

The flavones are characterized by the following basic structure:

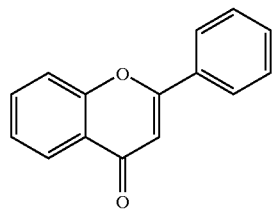

The 3-hydroxyflavones (flavonoles) are characterized by the following basic structure:

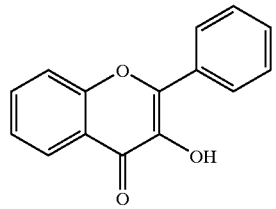

The isoflavones are characterized by the following basic structure:

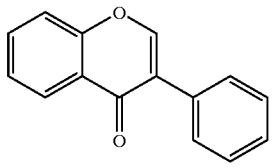

The aurones are characterized by the following basic structure:

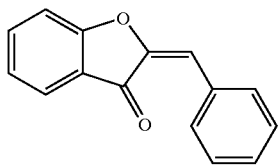

The coumaranones are characterized by the following basic structure:

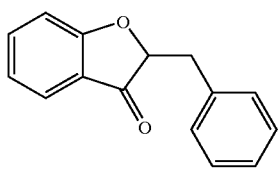

Preferably the flavonoides and coumaranones are selected from the compounds of formula (1):
Formel (1):

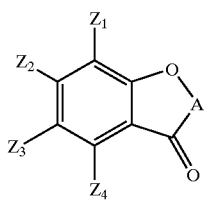

(1)

wherein:

$Z_1$ to $Z_4$ independently each represent H, OH, alkoxy, hydroxyalkoxy, mono- or oligoglycoside radicals, wherein the alkoxy and hydroxyalkoxy groups can be branched and straight and contain from 1 to 18 carbon atoms and wherein also sulfate or phosphate ran be bound to the hydroxy groups of the named radicals, A is selected from the group consisting of the partial formulae (1A), (1B) and (1C)

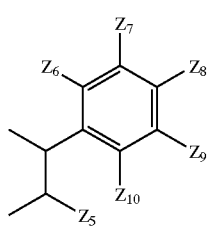

(1A)

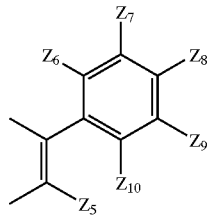

(1B)

(1C)

$Z_5$ represents H, OH or OR,

R represents a mono or oligoglyooside radical, $Z_6$ to $Z_{10}$ have the meanings of the radicals $Z_1$ to $Z_4$ and

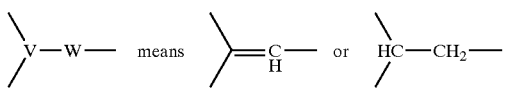

The alkoxy groups are preferably linear and contain from 1 to 12 preferably from 1 to 8 carbon atoms. These groups thus correspond to the formula —O—$(CH_2)_m$—H, wherein m is 1,2,3,4,5,6,7 or 8 and in particular 1 to 5.

The hydroxyalkoxy groups are preferably linear and contain from 2 to 12, preferably from 2 to 8 carbon atoms. These groups thus correspond to the formula —O—$(CH_2)_n$—OH, wherein n is 2,3,4,5,6,7 or 8, in particular 2 to 5 and particularly preferred 2.

The mono- and oligoglycoside radicals preferably are constituted of 1 to 3 glycoside units. Preferably these units are selected from the group consisting of hexosyl radicals, in particular rhamnosyl radicals and glucosyl radicals. But also other hexosyl radicals, for example allosyl, altrosyl, galactosyl, gulosyl, idosyl, mannosyl and talosyl can be optionally used with advantage. It can also be advantageous to use pentosyl radicals.

In a preferred embodiment $Z_1$ and $Z_3$ represent H, $Z_2$ and $Z_4$ have another meaning than H, in particular represent OH, methoxy, ethoxy or 2-hydroxyethoxy, $Z_5$ represents H, OH or a glycoside radical being constituted of 1 to 3, preferably 1 or 2 glycoside units, $Z_6$, $Z_9$ and $Z_{10}$ represent H and $Z_7$ and $Z_8$ have another meaning than H, in particular represent OH, methoxy, ethoxy or 2-hydroxyethoxy.

Particularly preferred compounds are represented by the following general formula:

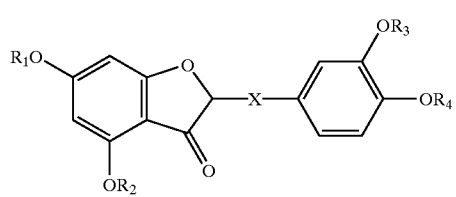

wherein:

—X— represents a single bond, —$CH_2$— or =CH— and $R_1$, $R_2$, $R_3$ and $R_4$ which can be identical or different, independently represent

H, straight or branched $C_1$–$C_{12}$-alkyl groups and/or -alkylcarbonyl groups, straight or branched $C_{13}$–$C_{12}$-alkenyl groups and/or -alkenylcarbonyl groups, straight or branched $C_1$–$C_{12}$-hydroxyalkyl- and/or -hydroxyalkylcarbonyl groups wherein the hydroxy group can be bound to a primary or secondary carbon atom of the chain and wherein the alkyl chain can also be interrupted by oxygen, $C_3$–$C_{10}$cycloalkyl- and/or -cycloalkylcarbonyl groups and also be bridged (linked) by —$(CH_2)_n$-groups wherein n is 1 to 3, aryl groups and/or arylcarbonyl groups heteroaryl groups and/or heteroarylcarbonyl groups, wherein these groups can be substituted by alkyl, hydroxy, alkoxy, amino, mono and dialkylamino, sulfonic acid, carboxylic and/or halogen groups, mono- or oligoglycoside radicals,

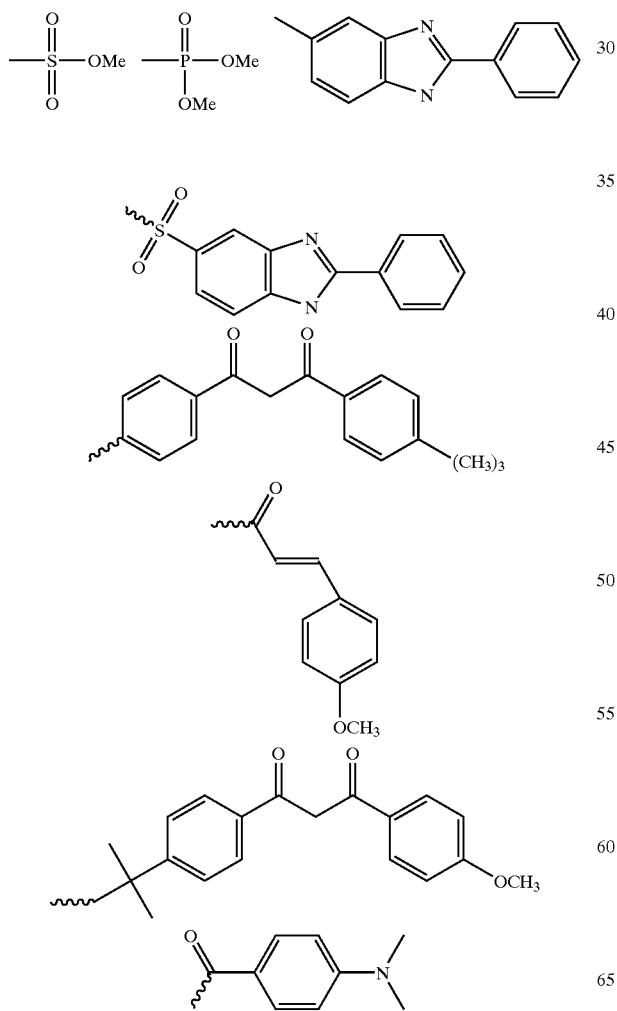

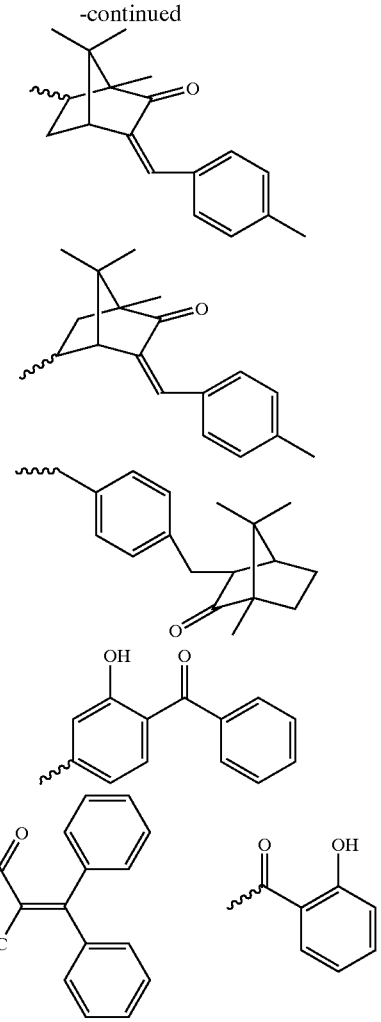

wherein $R^5$ represents tert.-butyl or isopropyl and

Me represents a proton or an alkaline metal ion, in particular a potassium ion.

The radicals thus can be bound to the basic body as ethers or as esters.

In a further preferred embodiment the flavonoides are selected from the following compounds; 4,6,3',4'-tetrahydroxyauron, quercetin, rutin, isoquercetin, anthocyanidin (cyanidin), eriodictyol, taxifolin, luteolin, trishydroxyethylquercetin (troxequercetin), trishydroxyethylrutin (troxerutin), trishydroxyethylisoquercetin (troxeisoquercetin) as well as trishydroxyethylluteolin (troxeluteolin).

Preferred flavonoides are in particular rutin and troxerutin. Particularly preferred is troxerutin.

Preferred among the coumaranones is 4,6,3',4'-tetrahydroxybenzyl-coumaranone-3.

Suitable repellants comprise amides and derivatives thereof.

Suitable preservatives comprise benzoic acid and salts thereof (such as sodium benzoate), methylparaben, ethylparaben, propylparaben, sorbic acid and salts thereof (such as potassium sorbate) as well as salicylic acid and salts thereof (such as sodium salicylate).

The active substance used according the invention can also be an antiphlogistic substance.

The active substance used according to the invention preferably is soluble in oil and/or water and by the covalent bond to an inorganic pigment it is transferred into a condition in which it can no more penetrate into the skin.

According to the invention it is preferred that the spacer group comprises a reactive metal centre.

The conjugate of the invention is preferably represented by the following formula (I):

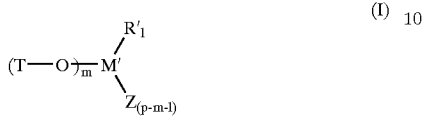

wherein;

T represents an oxide of an element, selected from the group Si, B, Al, Fe, Sn, Ti and Zr, or a mixed oxide of these elements being present in the core of the pigment;

M' represents a reactive metal centre comprising an element of the groups 3A, 4A, 3B, 4B, 5 B or 6B of the periodic table of elements;

$R^1$ represents the covalently bound active substance-group;

Z represents, identical or different, H, OH, a halogen atom, selected from F, Cl, Br, and/or an organic radical, selected from A, OA, ACOO, $NA_2$, SA, saturated or unsaturated cycloalkyl having up to 6 carbon atoms, an heterocyclic or aromatic radical Ar, wherein y is 0,1,2,3,4, A represents a straight, branched, saturated or unsaturated alkyl radical having from 1 to 8 carbon atoms and Ar represents substituted or unsubstituted phenyl, naphthyl, pyridyl, pyrimidinyl, thiophenyl, furanyl, wherein the substituents may be A, OA, COGH, COOA, Cl or F;

p represents the maximally possible valence of M';

m is 1, 2 or 3 and l is $\leq$(p-m).

Further preferred examples of T comprise the oxides and mixed oxides mentioned above as preferred inorganic pigments and mixed pigments.

This means with other words, that the conjugate of the invention of formula (I) in particular is represented by the following formulae (II), (III) and (IV):

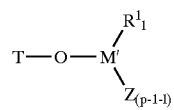

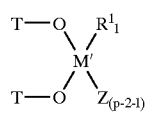

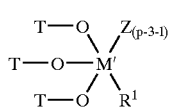

In this case the spacer group is represented by —(O)$_m$—M'.

Preferably T represents an oxide of an element, selected from the group Si, B. Al, Fe, Sn, Ti and Zr or a mixed oxide of these elements.

M' preferably represents Al, Si, Ti or Zr.

Z preferably represents H, OH, a halogen atom, A, OA or ACOO.

The conjugate of the invention in particular is preferably represented by the formula (II) or (III).

Preferred examples of $R^1$ comprise:

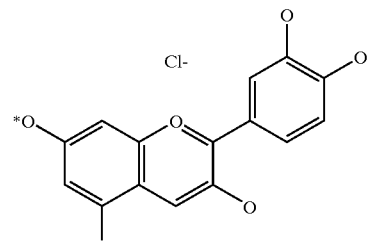

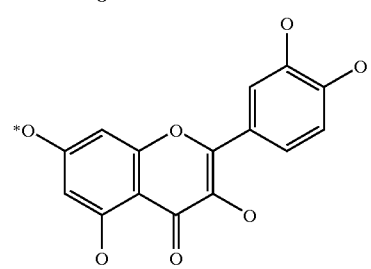

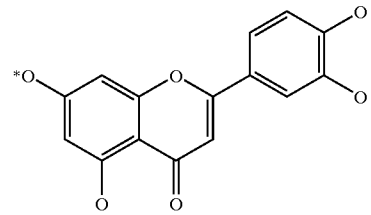

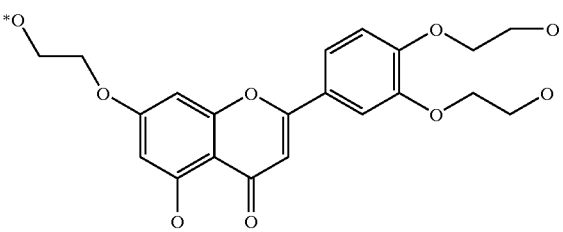

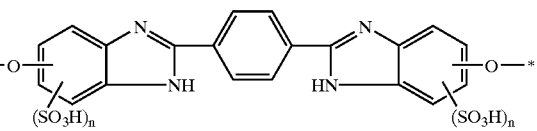

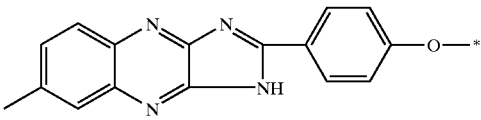

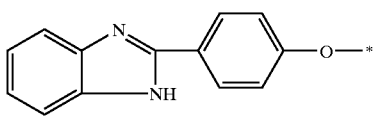
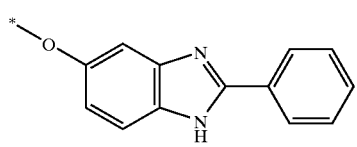
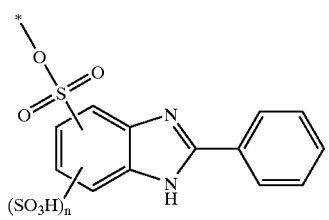
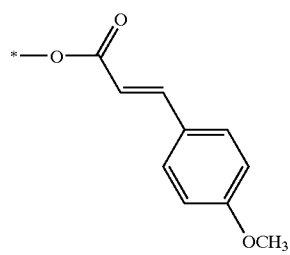
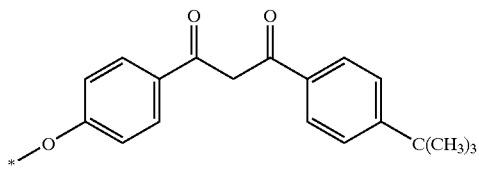
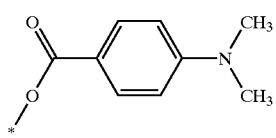
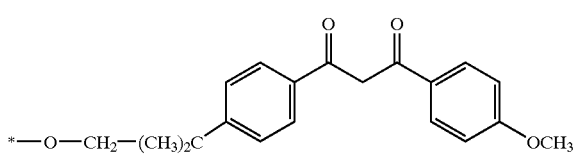
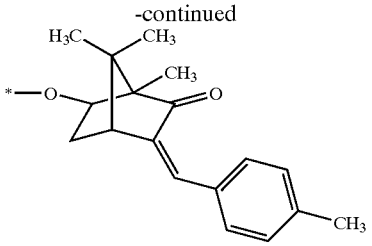
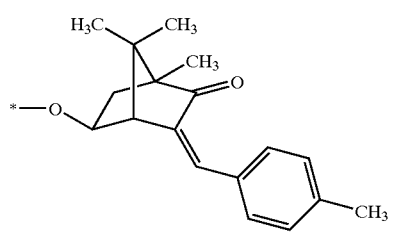
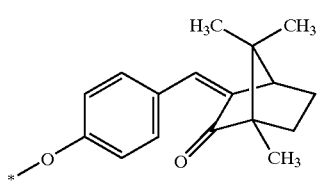
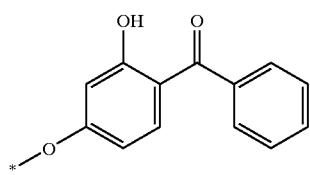
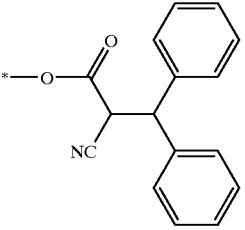
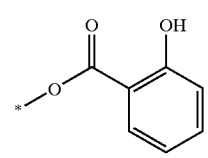
wherein n is 0, 1 or 2 and * represents the bond to the spacer group.
In the compounds mentioned above the bonding to a spacer group is through an oxygen atom. However, the bonding to the spacer group can also be through another linking group such as through the groups —NH—, —OCH$_2$O— or —OCH$_2$CH$_2$O—.
Preferred examples of the conjugate of the invention comprise.

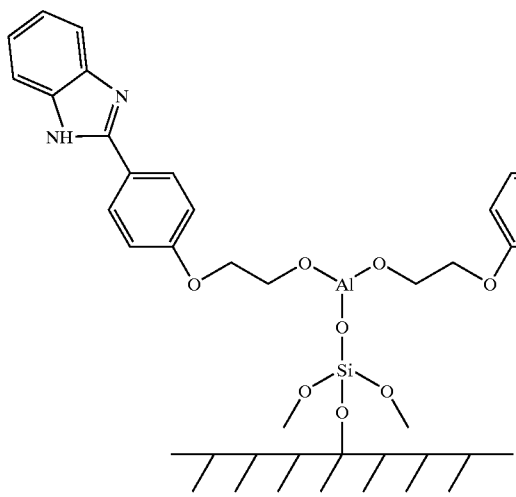
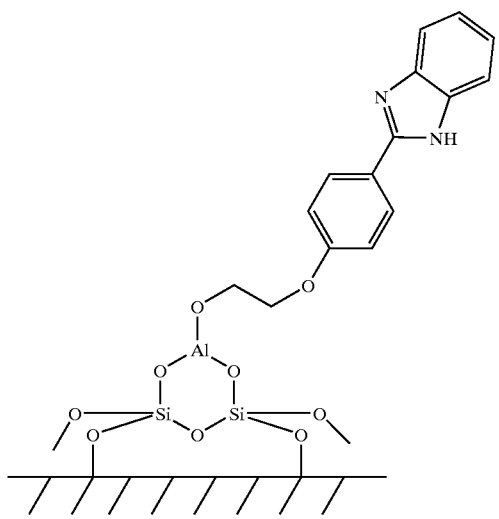
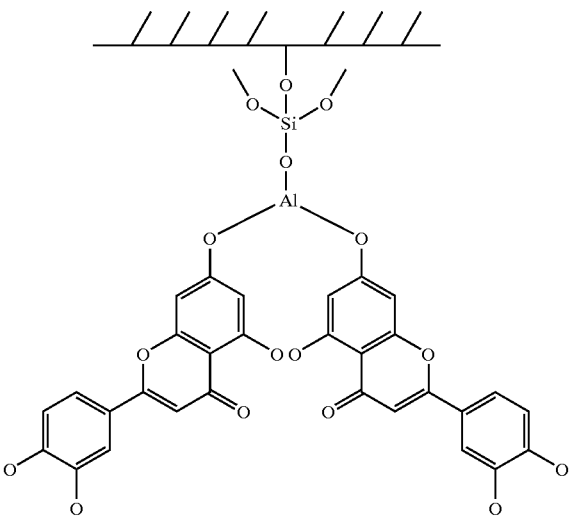
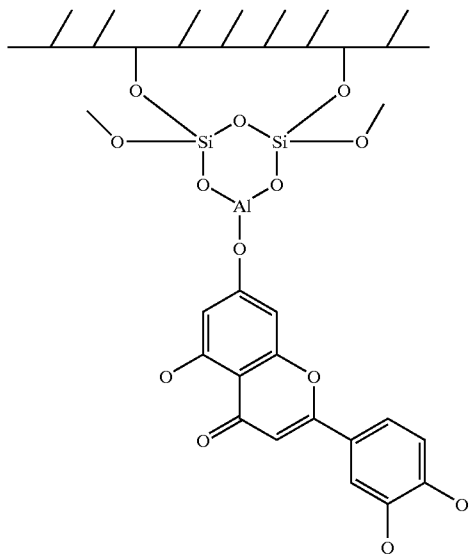
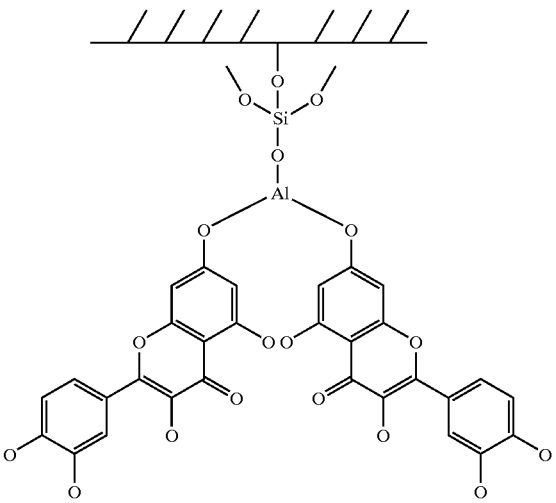

-continued
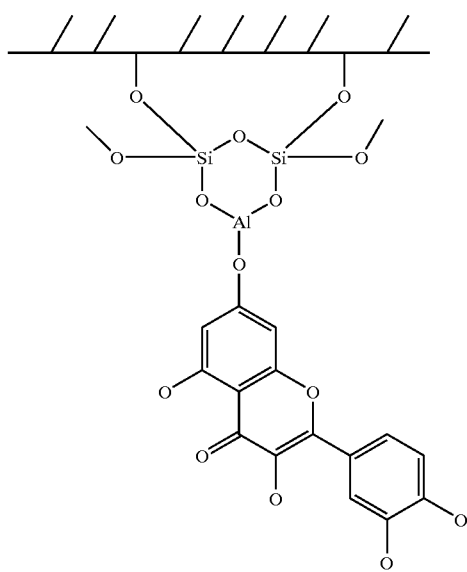
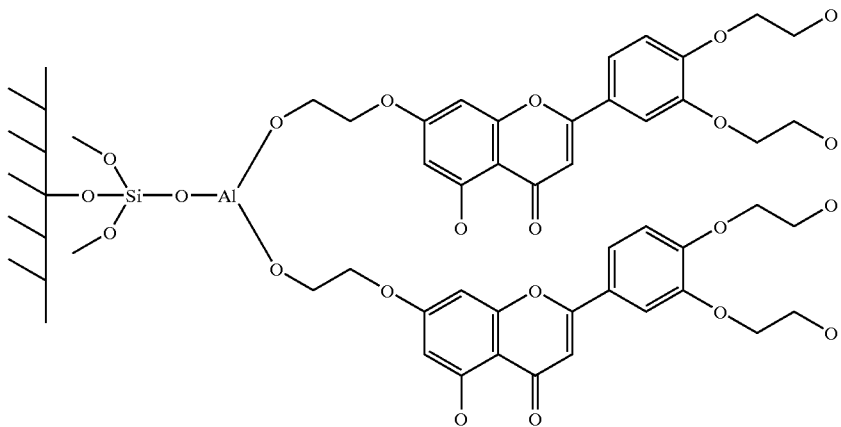
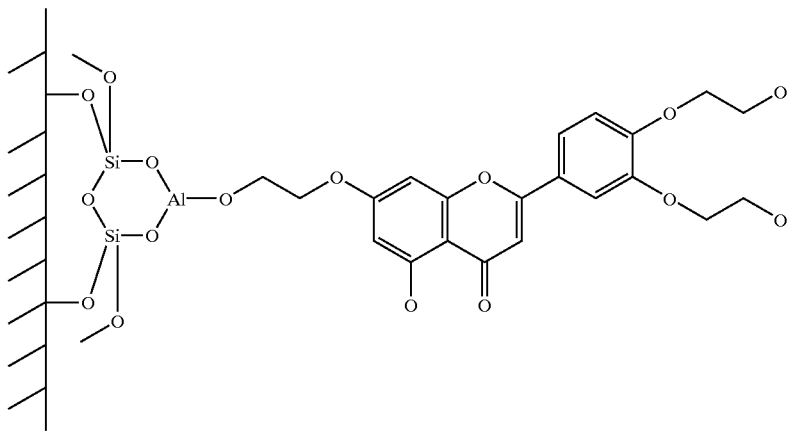

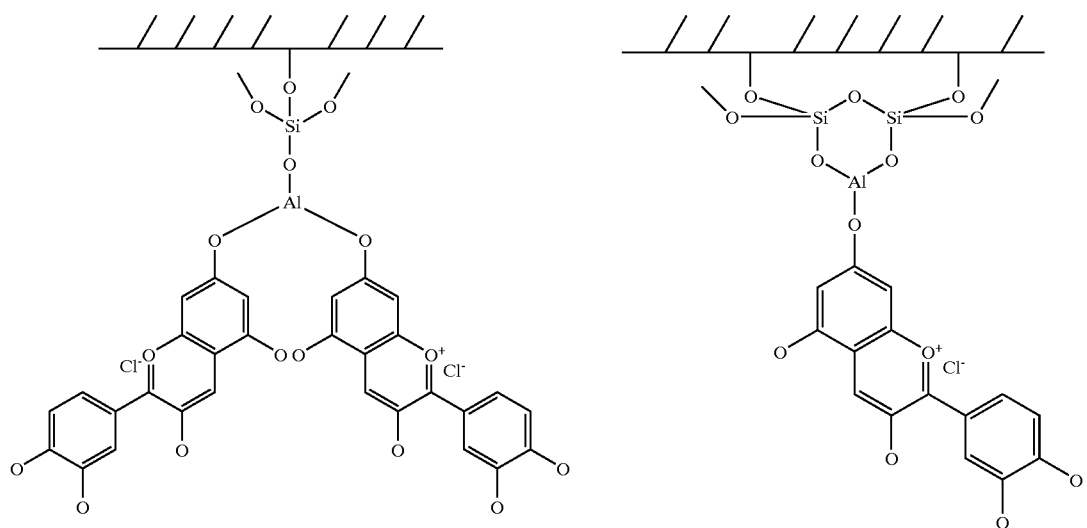
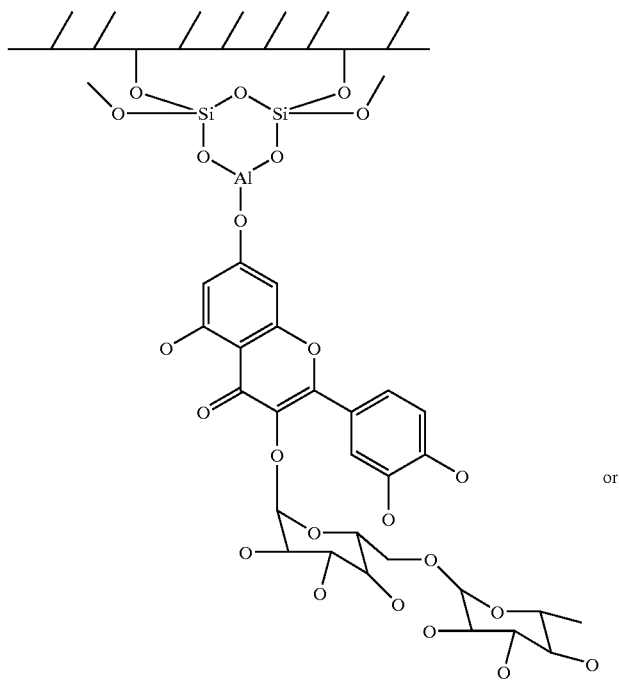
or

-continued

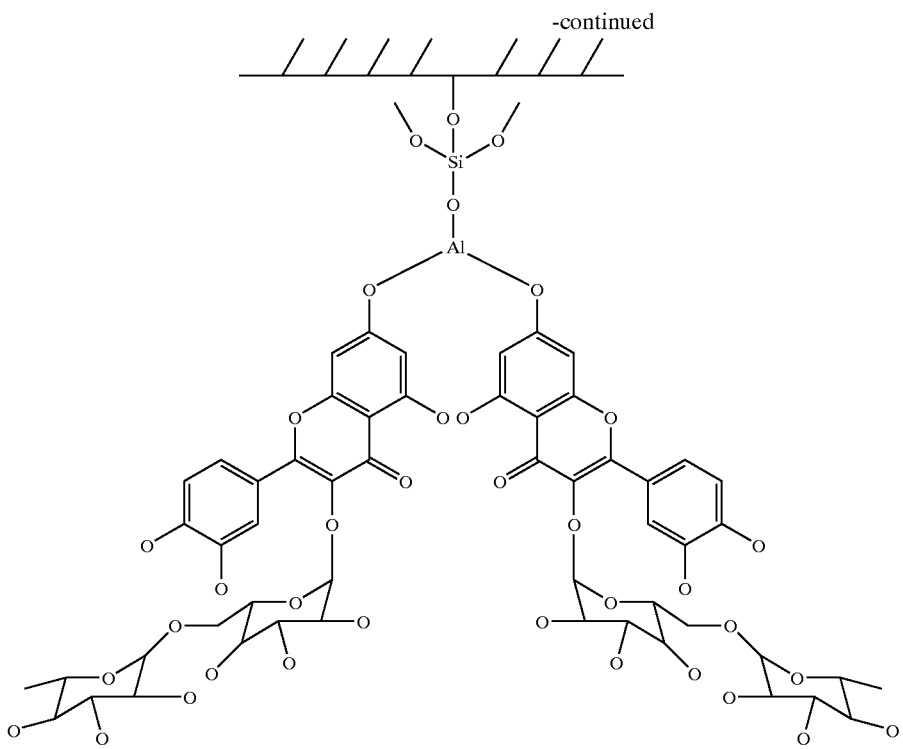

wherein the structures

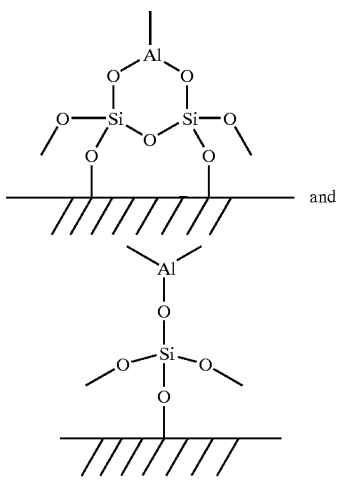

and represent the inorganic support (solid), in this case a silicon dioxide, which is used in the form of a aluminumorganyl compound for formation of the conjugate wit the UV filter. However, the conjugates are not restricted to these structures.

Preferred conjugates are those wherein at least two molecules of active substance are bonded to a reactive metal centre M'.

For preparing the conjugate of the invention the active substance can also be covalently bound through an organic linking group to an inorganic support. In the frame of the present invention the expression "organic linking group" means a monomeric or oligomeric compound group, however, no polymeric group, such as —O(CH$_2$CH$_2$O)$_n$—, wherein n is a number in the range of from 1 to 20. n preferably represents 1 or 2.

The conjugate of the invention can be prepared by first modifying the inorganic pigment and substrate, respectively, with a metalorganic compound to form a support material having a reactive surface. This reactive surface then reacts corresponding to its chemical nature with reactive groups of the active substance. These reactive groups can be for example active hydrogen (derived from carbon atom oder hetero atom-containing groups) or a metal derivative of a nucleophile.

A typical process is described for example in DE-A-198 02 753. Therein the inorganic pigment exhibiting OH oder OM groups at its surface, wherein M corresponds to an alkaline metal or an alkaline earth metal atom equivalent, is reacted with a metal derivative. The metal derivative is a metal halogenide, a metal organyl or a metal hydride or a mixture thereof wherein the metal ion is defined like M', halogen is defined as mentioned above and the organyl radical is defined as the organic radical of Z.

As metal halogenes or hydrides compounds can be used wherein one or more of the organic radicals is replaced by a halogen atom and/or by H.

Correspondingly, the metal derivative is represented by formula M'(Z)$_p$ with the provision that the metal derivative contains at least a fugitive group, i.e. a halogen atom or an alkoxy, acyloxy or organylsulfate radical. Thus, the obtained surface-active inorganic pigments are represented by general formula (V) and formulae (VI), (VII) or (VIII), respectively:

$$(T-O))_m-M'-Z_{(p-m)} \qquad (V)$$

$$T-O-M'-[Z]_{p-1} \qquad (VI)$$

-continued

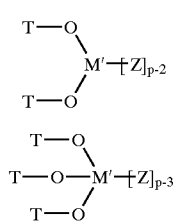

These intermediate product then can be covalently bound to the active substance-radical $R^1$. Usually the bonding occurs through nucleophilic substitution.

As a result, the above intermediate product is reacted with ionic nucleophiles (IX) or with nucleophiles (X) which are substituted by hydrogen:

$R^{1\ominus}$ (IX)

$R^1$—H (X)

The conjugate of the invention can be obtained carding to the following reaction scheme:

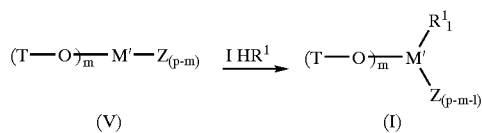

In particular, the following reactions can be carried out:

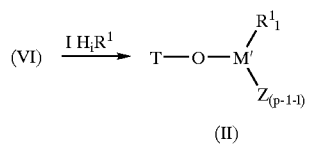

wherein I = 1–3

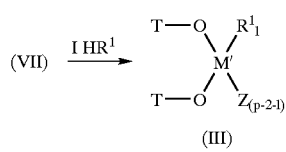

wherein I = 1–2 and

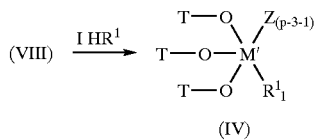

wherein I = 1

The synthesis of the conjugate of the invention can be carried out in an inert solvent selected in correspondence to the used starting materials or by vapor deposition of the active substance on the reactive surface of the pigment substrate.

The number of the reactive groups, such as hydroxy groups, at the surface of the inorganic pigment can be increased by using the process as described in DE-A-198 02 753.

Inorganic support materials depending on the chemical structure exhibit at the surface a more or less large number of reactive OH groups which can form a chemical bond. This number is for example about 4.4 to $8.5/nm^2$ for completely hydroxylated $SiO_2$ monospheres (H. P. Boehm, "Angew. Chem." 78, 617 (1986)). These values were confirmed by J. Kratochvila et al., "Journal of Non-Crystalline Solids" 143, 14–20 (1992). At a bonding distance of about 0.16 nm for the Si—O bond and at an angle of 150° for the Si—O—Si angle there are about 13 Si atoms/$nm^2$ at the surface of the $SiO_2$ monospheres. This means, that in the superficial monolayer a maximum of 13 Si—OH groups can be present with an additional triple valence bonding of the Si through the oxidic oxygen bridges. However, normally in $SiO_2$ monospheres which have been dried at room temperature, only 4 Si—OH groups can be expected (see Boehm and Kratochvila).

In order to obtain an number of active Si—OH groups as large as possible on the $SiO_2$ monospheres per weight unit the surfaces of the $SiO_2$ monospheres can be increased in the form of pores, gaps and/or by particle diameters which are as small as possible. By increasing the number of the Si—OH groups by saturating with water or steam no sufficient solution is obtained, since the water additionally adsorbed at the surface causes hydrolysis of most of the chemisorptive bonds of the surface to ligands. On the other hand, intensive drying leads to a decrease of the number of the Si—OH groups to lower than 2 per $nm^2$.

According to the process described in DE-A-198 02 753 for example an oxide or silicate in an inert aprotic solvent such as THF, DMF, cyclohexane or toluene is treated with a strongly basic reagent such as an alkaline metal or alkaline earth metal hydroxide, a hydride or an alcoholate in order to split the superficial oxide bondings of the oxide or silicate, and then the treated oxide or silicate is treated with an inorganic or organic acid to form additional hydroxy groups.

When inorganic pigments used according to the invention are treated according to this process, the bond density of the active substances to the surface of the inorganic pigment can be increased.

The particle size of the conjugate of the invention is not limited to a certain particle size; normally, however, it lies within a range of from 1 nm to 250 μm, preferably in a range of from 1 nm bis 1 μm and particularly preferably in a range of from 5 nm to 100 nm, in order to ensure an optimal distribution on the skin.

The conjugate of the invention can be dried after its preparation and then it can be introduced into the dermatological or cosmetic composition or it can be introduced into the dermatological or cosmetic composition in the form of a dispersion, for example dispersed in a cosmetic oil or liquid light filter.

Suitable oil components comprise natural and synthetic substances like paraffin oil, glycerylstearate, isopropylmyristate, diisopropyladipate, 2-ethylhexanoic acid-acetylstearylester, hydrogenated polyisobutene, vaseline, caprylic acid/-caprinic acid-triglycerides, microcrystalline wax, lanolin, mineral oils, mineral waxes, esters of fatty acids with alcohols like isopropanol, propyleneglycol or glycerine, alkylbenzoates, silicone oils like dimethylpolysiloxanes, diethylpolysiloxanes or diphenylpolysiloxanes, stearic acid, light filters which are present in liquid form as well as vitamin K1, Preferred examples comprise ethylbutylacetyl-aminopropionate (IR 3535™), butyleneglycol-dicaprylate/dicaprinate (Miglyol 8810), propyleneglycol-dicaprylate-dicaprinate, $C_{12-15}$-alkylbenzoates, isopropylmyristate, caprylic acid/caprinic acid-triglycerides, octylpalmitate, almond oil, avocado oil, jojoba oil, isostearylisostearate, octyldodecanol, dibulyladipate (Cetiol B), coco acid-glycerides (Myritol 331), dicaprilylether (Cetiol OE), isostearyl-neopentanoate (Ceraphyl 375). $C_{12-15}$-alkyllactates (Ceraphyl 41), dioctylmalate (Ceraphyl 45) as well as the liquid light filters Euaolex® 2292, Eusolex® OCR, Eusolex® 6007, Eusolex® HMS and Eusolex® OS.

The dermatological or cosmetic composition of the invention contains the conjugate described above or a combination of the conjugates described above with at least one cosmetically, pharmaceutically and/or dermatologically compatible vehicle and/or adjuvant. Of course, the dermatological or cosmetic composition can also contain the conjugate of the invention in combination with other active substances like organic or inorganic UVA and UVB filters, IR or VIS filters or in combination with repellants which do not form conjugates such as N,N-diethyl-3-methyl-benzamide, 3-[N-n-butyl-N-acetyl]-aminopropionic acid ethylester (IR3535®) or N,N-caprylic acid diethylamide (IR790®) or in combination with preservatives which do not form conjugates such as benzalkoniumchloride, cetylpyridiniumchloride or cetrimoniumchloride. Particularly preferred is the combination with further UV filters comprising the unbound light filters described above or mixtures thereof. The ratio between the bound active substances (i.e. the active substances which are bound to pigments) and the unbound active substances (i.e. the active substances which are not bound to pigments) preferably lies within a range of from 1:10 to 10:1 and particularly preferred in a range of from 1:5 to 5:1. For example, light filters bound to pigments can be combined with unbound light filters.

The dermatological or cosmetic composition of the invention contains the conjugate of the invention optionally in combination with further cosmetic substances, preferably in an amount in the range of from 0.05 to 30% by weight, particularly preferred in an amount in the range of from 0.5 bis 10% by weight and especially preferred in an amount in the range of from 0.5 to 6% by weight, based on the total weight of the dermatological or cosmetic composition.

Definitions of the Cosmetic Substances

Examples of inorganic UV filters comprise coated titanium dioxide (e.g. Eusolex® T-2000 or Eusolex® T-AQUA), zinc oxides (e.g. Sachtotec®), iron oxides and cerium oxides. These inorganic UV filters are incorporated into the dermatological or cosmetic compositions of the invention usually in an amount of from 0.5 to 10% by weight, preferably from 2 to 5% by weight.

Examples of vehicles and adjuvants comprise thickening agents, softening agents, humectants, surfactants, emulgators, preservatives, antifoaming agents, perfums, fats and waxes, lanolin, propellants, stabilizers, antioxidants, bactericides, dyes and/or pigments which color the formulation per se or the skin, film forming agents, odor improvers, complexing agents and other usual additives used in cosmetics.

As dispersant and solubilizer, respectively, a cosmetic oil, a wax or another fatty body, an alcohol or a polyol or mixtures thereof can be used. Particularly preferred alcohols or polyols are ethanol, i-propanol, propylenglycol, glycerine and sorbitol.

As emulgators preferably known W/O emulgators, but also O/W emulgators like polyglycerine esters, sorbitane esters or partially esterified glycerides can be used.

Typical examples of fats comprise glycerides and as waxes for example bees wax, carnauba wax, paraffin wax or microwaxes can be used, optionally in combination with hydrophilic waxes.

As stabilizers metal salts of fatty acid like magnesium, aluminum and/or Zinc stearate can be used.

Suitable thickening agents are for example cross-linked polyacrylic acids and derivatives thereof, polysaccharides, in particular xanthan gum, guar-guar, agar-agar, alginates and tyloses, carboxymethylcellulose and hydroxyethyl-cellulose, further fatty alcohols, monoglycerides and fatty acids, polyacrylates, polyvinylalcohol and polyvinylpyrrolidone.

Usable film forming agents comprise hydrocolloides, such as chitosan, microcrystalline chitosan or quaternary chitosan, polyvinylpyrrolidone, vinylpyrrolidone-vinylacetate copolymers, polymers of the acrylic acid series, quaternary cellulose derivatives and similar compounds.

Suitable preservatives are for example formaldehyde solutions, p-hydroxy-benzoate or sorbic acid.

As nacreous agents for example glycoldistearic acid esters such as ethylene-glycol-distearate, but also fatty acids and fatty acid monoglycolesters are usable.

As dyes substances which are suitable and admitted for cosmetic purposes can be used as listed for example in the publication "Kosmetische Farbemittel" of the Farbstoffkommission der Deutschen Forschungsgemeinschaft, published in Verlag Chemie. Weinheim, 1984.

As antioxidants for example amino acids, imidazoles, peptides, carotinoides, α-hydroxy acids, unsaturated fatty acids, vitamin A, C and/or E and suitable derivatives of these substances can be used as well as zinc and its compounds (like $ZnO$, $ZnSO_4$) or selenium and its compounds (like selenium methionine). Preferred antioxidants comprise the substances mentioned above having anti-oxidative properties, where flavonoides, coumaranones, vitamins and BHT are preferred.

Mixtures of antioxidants can also be used in the dermatological and cosmetic compositions of the invention. Known and commercially available mixtures comprise mixtures which contain as active ingredients lecithin, L-(+)-ascorbylpalmitate and citric acid (e.g. Oxynex® AP), natural tocopherols, L-(+)-ascorbylpalmitate, L-(+-ascorbic acid and citric acid (e.g. Oxynex® K LIQUID), tocopherol extracts from natural sources, L-(+)-ascorbylpalmitate, L-(+)-ascorbic acid and citric acid (e.g. Oxynex® L LIQUID), DL-α-tocopherol, L-(+)-ascorbylpalmitate, citric acid and lecithin (e.g. Oxynex® LM) or BHT, L-(+)-ascorbylpalmitate and citric acid (e.g. Oxynex® 2004).

In a preferred embodiment the flavonoides are selected from the following compounds: 4,6,3',4'-tetrahydroxyauron, quercetin, rutin, isoquercetin, anthocyanidin (cyanidin), eriodictyol, taxifolin, luteolin, trishydroxyethylquercetin (troxequercetin), trishydroxyethylrutin (troxerutin), trishydroxyethyl-isoquercetin (troxeisoquercetin), trishydroxyethylluteolin (troxeluteolin) as well as sulfates and phosphates.

Among the flavonoides rutin and troxerutin are particularly preferred. Especially preferred is troxerutin.

Among the coumaranones 4,6,3',4'-tetrahydroxy-benzylcoumaranone-3 as well as it salts (sulfate, phosphate) are preferred.

The dermatological or cosmetic composition of the invention can contain as further ingredients vitamins. Preferably vitamins and vitamin derivatives selected from vitamin A, vitamin A propionate, vitamin A palmitate, Vitamin A acetate, retinol, vitamin B, thiaminechloride-hydrochloride (vitamin $B^1$), riboflavin (vitamin $B_2$), nicotic acid amide, vitamin C (ascorbic acid), vitamin D, ergocalciferol (vitamin $D_2$), vitamin E, DL-α-tocopherol, tocopherol E acetate, tocopherol-hydrogensuccinate, vitamin $K_1$, esculin (active substance of vitamin P), thiamine (vitamin $B_1$), nicotinic acid (niacin), pyridoxin, pyridoxal, pyridoxamine, (vitamin $B_6$), panthothenic acid, biotin, folic acid and cobalamin (vitamin $B_{12}$), are contained in the dermatological or cosmetic compositions of the invention, particularly preferred are vitamin A palmitate, vitamin C, DL-α-tocopherol, tocopherol E acetate, nicotinic acid, pantothenic acid and biotin.

Optionally the dermatological or cosmetic compositions of the invention can also contain one oder more chemical substances having self-tanning properties.

As chemical substances having self-tanning properties all natural and synthetic substances which are suitable for the preparation of cosmetic formulations and which are known to the expert can be used. These can be both plant extracts and synthetic self-tanning agents like dihydroxyacetone or α-ketoles as well as crythrolose.

Application forms of the dermatological or cosmetic compositions of the invention comprise: suspensions, emulsions, fat sticks, pastes, ointments, creams or milk (O/W, W/O, O/W/O, W/O/W), lotions, powders, soaps, tenside containing cleansing preparations, oils, aerosols, sprays as well as oily-alcoholic, oily-aqueous or aqueous-alcoholic gels and solutions, respectively. Further application forms are for example sticks, shampoos and shower baths.

The aqueous phase of the dermatological or cosmetic compositions of the invention preferably contains alcohols, diols or polyols as well as ethers, preferably ethanol, isopropanol, 1,2-propandiol, propyleneglycol, glycerine, ethyleneglycol, ethyleneglycolmonoethyl- or -monobutylether or analogous products, further one or more thickener, such as silicon dioxide, aluminum silicates, polysaccharides and derivatives thereof, e.g. hyaluronic acid, xanthan gum, hydroxypropylmethylcellulose or a polyacrylate selected from the group of the so-called carbopoles.

Usable oil components comprise the oil components described above.

Ointments, pastes, creams and gels can contain usual vehicles such as animal and plant fats, waxes, paraffins, starch, tragacanth, cellulose derivatives, polyethylene glycols, silicones, bentonites, silicic acid, talc and rink oxide or mixtures of these substances.

Powders and sprays can contain usual vehicles such as milk sugar, talc, silicic acid, aluminum hydroxide, calcium silicate and polyamide powder or mixtures of these substances. Sprays can additionally contain usual propellants, such as chlorfluorohydrocarbons, propane/butane or dimethylether.

Solutions and emulsions can contain usual vehicles such as solvents, solubilizers and emulgators, e.g. water, ethanol, isopropanol, ethylcarbonate, ethylacetate, benzylalcohol, benzylbenzoate, propylene glycol, 1,3-butylglycol, oils, in particular cottonseed oil, peanut oil, cornseed oil, olive oil, castor oil and sesame oil, glycerine fatty acid esters, polyethylene glycols and fatty acid esters of sorbitan or mixtures of these substances.

Suspensions can contain usual vehicles such as liquid diluents, e.g. water, ethanol or propylene glycol, suspending agents like ethoxylated isostearyl alcohols, polyoxyethylene sorbitolesters and polyoxyethylene sorbitanesters, microcrystalline cellulose, aluminum-meta-hydroxide, bentonite, agar-agar and tragacanth or mixtures of these substances.

Soaps can contain usual vehicles like alkali salts of fatty acids, salts of fatty acid semi-esters, fatty acid proteinhydrolysates, isothionates, lanolin, fatty alcohol, plant oils, plant extacts, glycerine, sugars or mixtures of these substances.

Tenside containing cleansing products can contain usual vehicles such as salts of fatty alcohol sulfates, fatty alcohol ethersulfates, sulfosuccinic acid semi-esters, fatty acid proteinhydrolysates, isothionates, imidazolinium derivatives, methyltaurates, sarcosinates, fatty acid amideethersulfates, alkylamidobetaines, fatty alcohols, fatty acid glycerides, fatty acid diethanolamides, plant oils and synthetic oils, lanolin derivatives, ethoxylated glycerine fatty acid esters or mixtures of these substances.

Face and body oils can contain usual vehicles such as synthetic oils like fatty acid esters, fatty alcohols, silicone oils, natural oils like plant oils and oily plant extracts, paraffin oils, lanolin oils or mixtures of these substances. Preferred examples of such vehicles comprise the oil components mentioned above.

In a preferred embodiment the dermatological or cosmetic composition according to the invention is an emulsion being present in the form of a protection cream or milk and comprising in addition to the conjugate of the invention fatty alcohols, fatty acids, fatty acid esters, in particular triglycerides of fatty acids, lanolin, natural or synthetic oils or waxes and emulgators in the presence of water.

Further preferred embodiments are oily lotions based on natural or synthetic oils and waxes, lanolin, fatty acid esters, in particular triglycerides of fatty acids or oily-alcoholic lotions based on alcohols like ethanol or on glycols like propylene glycol and/or on polyols like glycerine and oils, waxes and fatty acid esters like triglycerides of fatty acids.

The dermatological or cosmetic composition of the invention can also have the form of an alcoholic gel containing one or more alcohols or polyols like ethanol, propylene glycol or glycerine and a thickener like diatomaceous earth. The oily-alcoholic gels can further contain a natural or synthetic oil or wax.

The solid sticks can contain natural or synthetic waxes and oils, fatty alcohols, fatty acids, fatty acid esters, lanolin and other fat bodies.

In the dermatological or cosmetic composition of the invention confectionated as an aerosol, generally usual propellants like alkanes, fluoroalkanes and chlorofluoroalkanes are used.

Further typical cosmetic application forms comprise lip sticks, lip care sticks, rouge, powder, emulsion and wax make-up as well as pre-sun and after-sun preparations.

All vehicles and adjuvants which can be used in the dermatological or cosmetic compositions of the invention are either known and commercially available or can be synthesized according to known processes.

The dermatological or cosmetic compositions of the invention can contain the vehicles and adjuvants mentioned above each in an amount in the range of from 0.001 to 30% by weight, preferably in an amount in the range of from 0.05 to 20% by weight and particularly preferably in an amount in the range of from 1 to 10% by weight.

The dermatological or cosmetic composition of the invention can be prepared by using processes which are known to an expert.

The conjugate of the invention can also be used to protect the skin, in particular to protect the Langerhans cells in the skin, to protect the DNA or to provide immunoprotection.

The conjugate of the invention can be used not only in cosmetics but also for example for the preparation of varnishes or security markings. In this case for example the group $R^1$ in the general formula mentioned above can be a fluorescent group which can be excited by UV light.

The following examples illustrate the invention. The used starting materials are either commercially available or can be synthesized in a known manner.

EXAMPLES

Example 1

Preparation of a Eusolex® 232/Monospher® 25-conjugate

A Eusolex® 232//Monospher® 25-conjugate has been prepared according to the following reaction scheme:

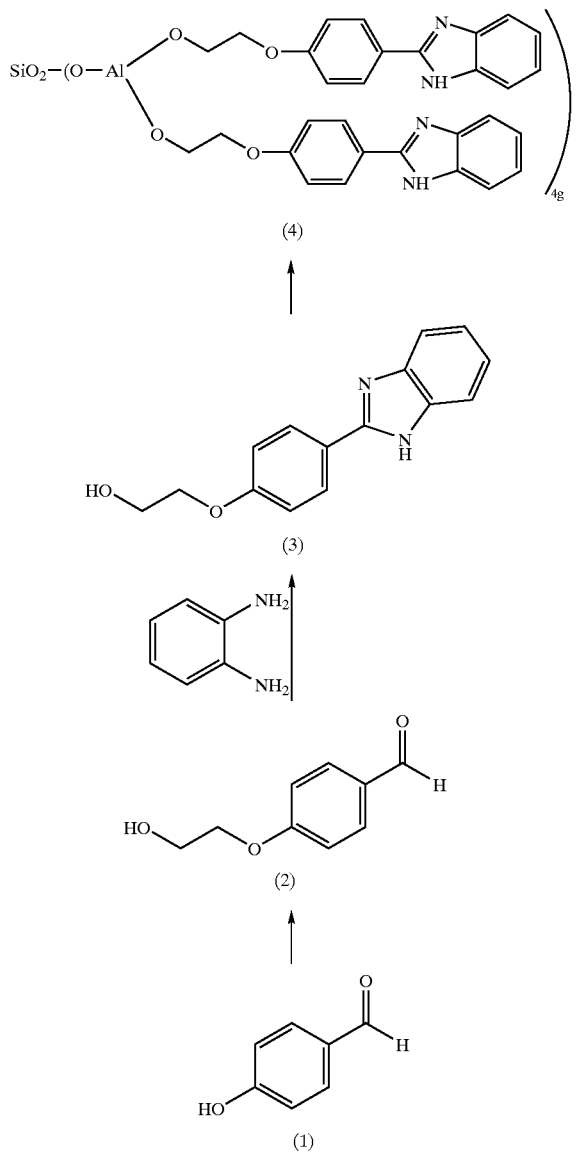

Preparation of 4-(2-hydroxyethoxybenzaldehyde (2)

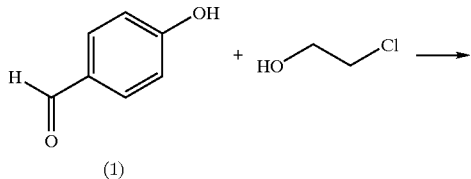

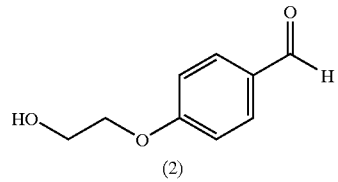

The apparatus used for carrying out the reaction was flushed with nitrogen in order to displace the air in the apparatus. Then 12.46 g of 4-hydroxybenzaldehyde (1) were suspended in 31.5 g of VE-water and added with 13.12 g of a 32% sodium hydroxide solution. The temperature increased to 36° C. 8.05 g of 2-chloroethanol were added to the suspension and heated under vigorous stirring to form a red-brown solution. The reaction mixture was stirred overnight at 82° C. (bath temperature 89 to 90° C.) and an emulsion was formed. The reaction time was 20 hours.

The reaction mixture was cooled to about 40° C. and added with 100 g of ethylacetate. The two-phases mixture (pH 10 to 11) was added with 17.5 g of 32% sodium hydroxide solution to adjust a pH of 13 to 14. After formation of the phases both phases were separated and the aqueous phases then were extracted with 50 g of a ethylacetate. The combined organic phases were washed with 50 g of saturated saline solution, filtrated on absorptive cotton and concentrated azeotropically in a rotary evaporator to form a brown oil.

The raw product was dissolved in 10 g of toluene/ethylacetate (1:1) under slight heating. The purification was carried out by filtration on a frit (diameter; 13 cm) by using 400 g of silica gel (Art. 7734, grain size, 0.063 to 0.200 mm; thickness of layer, 6.5 cm). The product was eluated with toluene/ethylacetate (1:1) The combined fractions were concentrated in a rotary evaporator until dryness.

Yield: 14.26 g of raw product 12.88 g of final product.

Preparation of (3)

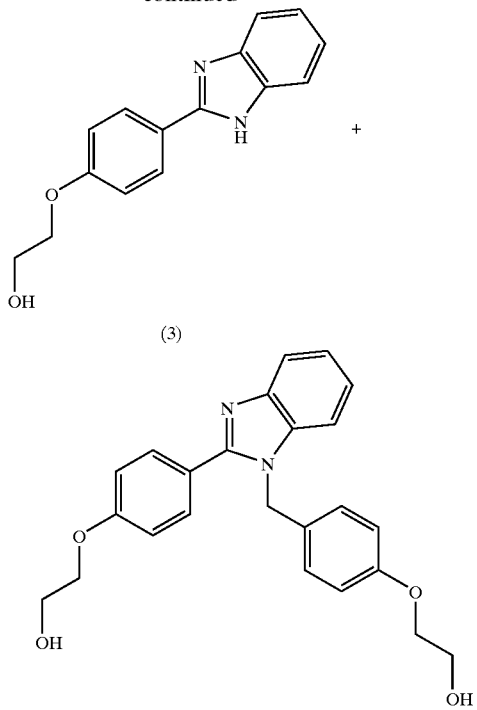

(3)

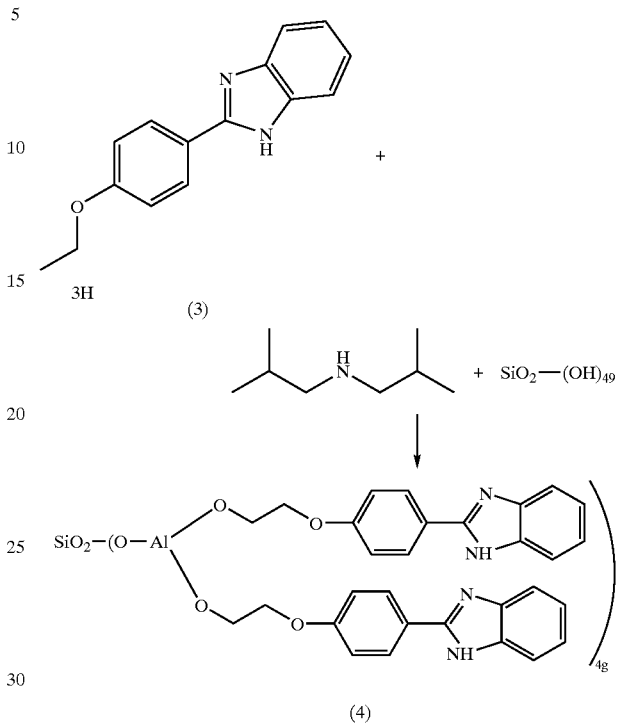

The apparatus used for carrying out the reaction was flushed with nitrogen to displace the air in the apparatus. Then 8.19 g of 1,2-phenylene diamine were introduced and added with a solution of 12.46 g of 4-(2-hydroxyethoxy)-benzaldehyde (2) in 38 g of 1-methyl-2-pyrrolidone. 21.33 g of sodium disulfite were introduced and the suspension was heated under vigorous stirring. After 14 minutes the reaction temperature (80° C.) was higher than the bath temperature and within further 2 minutes it increased up to 104.5° C. The color of the suspension changed several times between yellow, green and brown. The reaction mixture was stirred for further 90 minutes at an internal temperature of 103° C. (bath temperature of 103 to 104° C.).

The obtained suspension was cooled to 60° C. and within 15 minutes 135 g of VE-water were dropped in. The thick suspension/emulsion was slowly introduced into 500 g of VE-water at a temperature of 40° C. The fine suspension was stirred after 45 minutes at room temperature (27° C.). The raw crystallizate was isolated, washed in portions with 50 to 70 ml of VE-water, dried by suction and dried in vacuum overnight in an exsiccator at 45° C.

19 g of the raw product were suspended in 1000 g of methanol and heated within 45 minutes to reflux temperature (bath temperature: 76 to 80° C). After further 30 minutes a total of 200 g of methanol was added within 2 hours in portions. After 30 minutes a complete solution has been obtained and a slight precipitate was hot filtrated at 65 to 66° C. and disposed of after DC control. The reddish solution was concentrated in a rotary evaporator to 750 g and a formed new precipitate was filtered off. The solution in the rotary evaporator was further concentrated and, beginning with a volume of about 300 ml, an increasing product crystallization could be seen. The suspension was concentrated to 110 g. Thereafter the crystallizate (1. crystallizate) was isolated, portioned, washed with methanol and tried by suction. From the mother liquor at first a second crystallizate was isolated. The concentrated residue of mother liquor contained a mixture of product and a molar by-product. The crystallizates were dried in a vacuum exsiccator at 35° C.

Yield: 19.3 g of raw product
Final product (1. and 2. crystallizate): 16.02 g
Preparation of (4)

a) Production of Si—ONa Groups 30 g of silica gel spheres (Monospheres-Merck KGaA, Darmstadt) subjected to a water treatment followed by drying and having a diameter of 500 nm, a density of 2.0, a calculated surface area of 6 m$^2$/g and containing Si—OH groups, and water were added with 746 mg of NaH (3.11× 10$^{-2}$ mole) in 100 ml tetrahydrofuran at 30° C. A development of hydrogen occurred. From this volume of hydrogen and the amount of hydrogen released with trifluorosulfonic acid for control of the non-reacted NaH a total amount of 49 OH groups/nm$^2$ (4.9×10$^{-4}$ mol OH groups per gram silicagel) were obtained. This high value could be explained by a reaction of the water in the pores or gaps.

According to this pre-experiment 30 g of the above silica gel spheres in 100 ml of tetrahydrofuran were reacted with the calculated amount of NaH (353 mg=1.47×10$^{-2}$ mole) to form a silica gel having 49 Si—ONa groups per nm$^2$, in the following called "SiO$_2$—(ONa)$_{48}$". The spheres were filtered off and dried in vacuum. The tetrahydrofuran filtrate was neutral.

b) Conversion of the SiONa Groups into Si—OH Groups and Substitution of the SiOH Groups

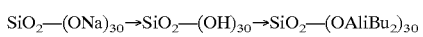

50 g of silica gel spheres (Monospheres 500, Merck KGaA) having a diameter of 500 nm and having 30 Si—ONa groups per mm$^2$ (SiO$_2$—ONa$_{30}$) were reacted with 1.39 ml (15.8 mmole) of CF$_3$SO$_3$H in 100 ml tetrahydrofuran to form SiO$_2$—(OH)$_{30}$. After filtration under nitrogen (Seitz pressure filter) and after washing with tetrahydrofuran the obtained spheres were reacted in 100 ml tetrahydrofuran with 15 mmole diisobutyl aluminiumhydride (12.5 ml of a 1.2 molar solution in toluene) while splitting off hydrogen and formation of $SiO_2$—$(OAl(iBu)_2)_{30}$.

c) Introduction of Organic Ligands 8 g of $SiO_2$—$(OAliBu_2)_{30}$ are stirred for 16 hours at 25° C. in 30 ml of tetrahydrofuran with (3). It is filtrated under nitrogen and washed with tetrahydrofuran to form (4).

Example 2

Preparation of a Cyanidin/Monospher® 500-conjugate

A cyanidin/Monospher® 500-conjugate was prepared in the following manner.

The apparatus used for carrying out the reaction was flushed with nitrogen and the air in the apparatus was displaced. Then Monospher® 500 (30 groups/nm$^2$) bonded to an aluminum compound (di-iso-butyl-Al) were introduced into the apparatus and slurried with THF to form a 10% dispersion. Thereafter the following compound was introduced into the dispersion:

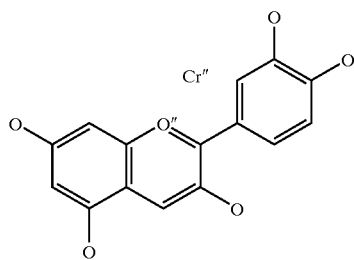

The obtained dark red reaction solution was stirred overnight at room temperature under a nitrogen atmosphere.

The next day the dark red reaction solution was filtered on a pressure filter. The filter residue was washed three times with each 20 ml of THF and/or pyrdine. The filter cake, a violet fine powder, was dried overnight in a vacuum exsiccator at room temperature and 150 mbar It could not be exactly cleared up which of the phenolic groups of the above compound has been reacted. It is also possible that two neighbouring OH groups had been reacted with the two isobutyl groups of an aluminum atom.

Parallel to this experiment a further batch was stirred overnight, whereby the Monospher® 500 bound to an aluminum compound (di-iso-butyl-Al) was replaced by non-bound Monospher® 500. The anthocyanidine was completely removed from Monospher® 500 by washing so that a white powder remained.

Example 3

Preparation of a Quercetin/Monospher® 500-conjugate

A quercetin/Monospher® 500-conjugate was prepared in the following manner.

The apparatus used for carrying out the reaction was flushed with nitrogen and the air in the apparatus was displaced. Then Monospher® 500 bound to an aluminum compound (di-iso-butyl-Al) was introduced into the apparatus and slurried with THF to form a 10% dispersion.

Thereafter the following compound was introduced into the dispersion:

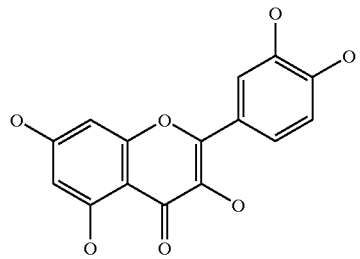

The obtained yellow reaction solution was stirred overnight at room temperature under a nitrogen atmosphere.

The next day the yellow reaction solution was filtered on a pressure filter. The filter residue was washed three times with each 20 ml THF and/or pyridine. The filter cake, a yellow fine powder, was dried overnight in a vacuum exsiccator at room temperature and 150 mbar.

Also in this case it could not be exactly cleared up which of the phenolic groups of the above compound had been reacted.

Parallel to this experiment a further batch was stirred overnight whereby the Monospher® 500 bound to an aluminum compound (di-iso-butyl-Al) was replaced by non-bound Monosphere® 500. The quercetin was completely removed from Monospher® 500 by washing so that a white powder remained.

Example 4

Preparation of a Luteolin/Monospher® 500-conjugate

A luteolin/Monospher® 500-conjugate was prepared in the following manner.

The apparatus used for carrying out the reaction was flushed with argon in order to displace the air in the apparatus. Then Monospher® 500 bound to an aluminum compound (di-iso-butyl-Al) was introduced into the apparatus and slurried with THF to form a 10% dispersion. Thereafter the following compound has been introduced into the dispersion:

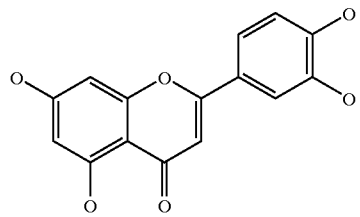

The obtained yellow reaction solution was stirred overnight at room temperature under an argon atmosphere.

The next day the yellow reaction solution was filtered on a pressure filter. The filter residue was washed three times with each 20 ml THF and/or pyridine. The filter cake, a light yellow fine powder, was dried overnight in a vacuum exsiccator at room temperature and 150 mbar.

Example 5

Preparation of a Triethoxyluteolin/Monospher® 500-conjugate

A triethoxyluteolin/Monospher® 500-conjugate was prepared in the following manner.

The apparatus used for carrying out the reaction was flushed with argon in order to replace the air in the apparatus. Then Monospher® 500 bound to an aluminum compound (di-iso-butyl-Al) was introduced into the apparatus and slurried with THF to form a 10% dispersion. Thereafter the following compound was introduced into the dispersion:

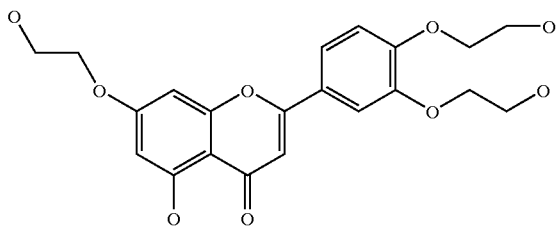

The obtained yellow reaction solution was stirred overnight at room temperature under an argon atmosphere.

The next day the yellow reaction solution was filtered an a pressure filter. The filter residue was washed three times With each 20 ml THF and/or pyridine. The filter cake, a light yellow fine powder, was dried overnight in a vacuum exsiccator at room temperature and 150 mbar.

Example 6
Preparation of a Rutin/Monospher® 500-conjugate

A rutin/Monospher® 500-conjugate was prepared in the following manner.

The apparatus used for carrying out the reaction was flushed with nitrogen in order to replace the air in the apparatus. Then Monospher® 500 bound to an aluminum compound (di-iso-butyl-Al) was introduced into the apparatus and slurried with THF to form a 10% dispersion. Thereafter the following compound was introduced into the dispersion:

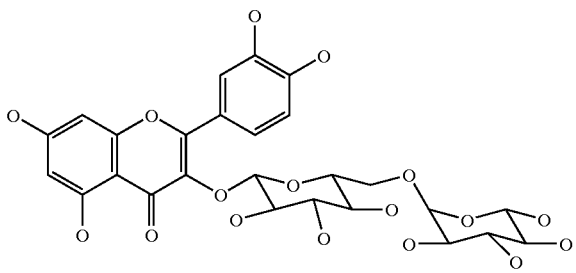

The obtained yellow reaction solution was stirred overnight at room temperature under a nitrogen atmosphere.

The next day the yellow reaction solution was filtered on a pressure filter. The ads filter residue was washed three times with each 20 ml THF and/or pyridine. The filter cake, a yellow fine powder, was dried overnight in a vacuum exsiccator at room temperature and 150 mbar.

Parallel to this experiment another batch was stirred overnight, whereby the Monospher® 500 bound to an aluminum compound (di-iso-butyl-Al) was replaced by non-bound Monospher® 500. The rutin was completely removed from Monospher® 500 by washing so that a with powder remained.

In the following examples of skin and sun protection formulations the Eusolex® 232/Monospher® 25-conjugate of example 1 has been used. However, it is also possible to use another conjugate of the invention.

Example 7
Examples of Skin Protection Formulations

| Skin protection lotion (O/W) | | | |
|---|---|---|---|
| raw material | INCl | | % by weight |
| A Monospher-conjugate | | (1) | 5.00 |
| Emulgator E 2155 | stearyl alcohol (and) Steareth-7 (and) Steareth-10 | (2) | 3.00 |
| Teginacid H | glyceryl stearate (and) Cateth-20 | (2) | 3.00 |
| Imwitor 900 | glyceryl stearate | (4) | 3.00 |
| Lunacera M | microwax | (6) | 1.00 |
| Luvitol EHO | cetearyl octanoate | (3) | 11.50 |
| Cetiol | oleyl oleate | (5) | 6.00 |
| Miglyol 812 neutral oil | caprylic/capric triglyceride | (4) | 6.00 |
| B propanediol-1,2 | propylene gylcol | (1) | 4.0 |
| allantoin | allantoin | (1) | 0.20 |
| preservative | | | q.s. |
| water, demineralized | aqua | | ad 100.00 |

Preparation

A phase A is heated to 75° C. and a phase B is heated to 80° C. The phase B is added to the phase A under slow stirring. The mixture is homogenized and cooled under stirring.

Remarks

Viscosity 9200 mPas (Brookfield RVT, Sp, C, 10 rpm) at 24° C.

pH 24° C.=5.0 preservative: 0.05% propyl-4-hydroxybenzoate 0.15% methyl-4-hydroxybenzoate

Supply Sources (1) Merck KGaA, Darmstadt
(2) Th. Goldschmidt, Essen
(3) BASF, Ludwigshafen
(4) Hüls, Troisdorf AG, Witten
(5) Henkel, Düsseldorf
(6) H. B. Fuller GmbH, Lüneburg

| Skin protection lotion (O/W) | | | |
|---|---|---|---|
| raw material | INCl | | % by weight |
| A Monospher-conjugate | | (1) | 1.00 |
| Emulgator E 2155 | stearyl alcohol (and) Steareth-7 (and) Steareth-10 | (2) | 3.00 |
| Teginacid H | glyceryl stearate (and) Cateth-20 | (2) | 3.00 |
| Imwitor 900 | glyceryl stearate | (4) | 3.00 |
| Lunacera M | microwax | (6) | 1.00 |
| Luvitol EHO | cetearyl octanoate | (3) | 11.50 |
| Cetiol | oleyl oleate | (5) | 7.00 |
| Miglyol 812 neutral oil | caprylic/capric triglyceride | (4) | 7.00 |
| B propanediol-1,2 | propylene gylcol | (1) | 4.00 |
| allantoin | allantoin | (1) | 0.20 |
| preservative | | | q.s. |
| water, demineralized | aqua | | ad 100.00 |

Preparation

The phase A ist heated to 75° C. and the phase B is heated to 80° C. The phase B is slowly added under stirring to the phase A. The mixture is homogenized and cooled under stirring.

Remarks
preservative:
0.05% propyl-4-hydroxybenzoate
0.15% methyl-4-hydroxybenzoate Supply Sources
(1) Merck KGaA, Darmstadt
(2) Th. Goldschmidt, Essen
(3) BASF, Ludwigshafen
(4) Hüls, Troisdorf A G, Witten
(5) Henkel, Düsseldorf
(6) H. B. Fuller GmbH, Lüneburg Beispiel 8: Examples of Sun Protection Formulations
Sun Protection Lotion Containing IR3535™ (O/W)

| raw material | INCl | | % by weight |
|---|---|---|---|
| Monospher-conjugate | | (1) | 3.00 |
| Eusolex 6300 | 4-methylbenzylidene camphor | (1) | 3.00 |
| IR 3535 ™ | ethyl-butylacetylaminopropionate | (1) | 10.00 |
| (-)-α-bisabolol | bisabolol | (1) | 0.30 |
| Montanov 68 | cetearyl alcohol (and) cetearyl glucosides | (2) | 4.00 |
| Myritol 312 | caprylic/capric triglyceride | (3) | 2.00 |
| Mirasil CM 5 | cyclomethicone | (4) | 2.00 |
| Mirasil DM 350 | dimethicone | (4) | 1.00 |
| B water, demineralized | aqua | | ad 100 |
| glycerine, 87% | glycerine | (1) | 3.00 |
| preservative | | | q.s. |
| C Rhodicare S | xanthan gum | (4) | 0.50 |

Preparation

The phases A and B are separately heated to 75° C. The phase C is added slowly at 75° C. while stirring to the phase B. The mixture is stirred until it is homogeneous. Thereafter the phase A is added to the mixture. The mixture is stirred until it is homogeneous and then cooled while stirring.

Remarks
preservative:
0.05% propyl-4-hydroxybenzoate
0.15% methyl-4-hydroxybenzoate
0.30% Germall 115 (ISP, Frechen)

Supply Sources
(1) Merck KgaA, Darmstadt
(2) Interorgana, Köln
(3) Henkel, KgaA, Düsseldorf
(4) Rhodia, Frankfurt Sun protection milk (O/W)

| raw material | INCl | | % by weight |
|---|---|---|---|
| A Monospher conjugate | | (1) | 4.00 |
| Eusolex 6300 | 4-methylbenzylidene camphor | (1) | 4.00 |
| Emulgator E 2155 | stearyl alcohol (and) Steareth-7 (and) Steareth-10 | (2) | 3.00 |
| Teginacid H | glyceryl stearate (and) Cateth-20 | (2) | 2.00 |
| Luvitol EHO | cetearyl octanoate | (3) | 14.00 |
| Imwitor 900 | glyceryl stearate | (4) | 3.00 |
| Cetiol | oleyl oleate | (5) | 6.00 |
| Luncacera M | microwax | (6) | 1.00 |
| Miglyol 812 neutral oil | caprylic/capric triglyceride | (4) | 4.00 |

-continued

Sun protection milk (O/W)

| raw material | INCl | | % by weight |
|---|---|---|---|
| B Eusolex 232 | phenylbenzimidazole sulfonic acid | (1) | 2.00 |
| tris(hydroxymethyl)-aminomethane | tromethamine | (1) | 1.07 |
| propanediol-1,2 | propylene glycol | (1) | 4.00 |
| allantoin | allantoin | (1) | 0.20 |
| preservative | | | q.s. |
| water, demineralized | aqua | | ad 100.00 |
| C Carbopol ETD 2050 | Carbomer ETD 2050 | (7) | 0.25 |
| water, demineralized | aqua | | 30.00 |
| D Tris(hydroxymethyl)-aminomethane | tromethamine | (1) | 0.25 |
| water, demineralized | aqua | | 4.00 |

Preparation

Carbopol ETD 2050 is dispersed homogeneously in water to obtain phase C. A phase D ist then introduced into phase C under homogenization. In order to neutralize Eusolex 232 the tris(hydroxymethyl)-aminomethane is dissolved in the water of phase B and Eusolex 232 is added under stirring. After completion of dissolution the residual ingredients of phase B are added and phase B is slowly introduced into phases C/D under homogenization. Phase A is dissolved by heating and is slowly added under homogenization.

Remarks
Preservative:
0.05% propyl-4-hydroxybenzoate
0.15% methyl-4-hydroxybenzoate Supply Sources
(1) Merck KGaA, Darmstadt
(2) Th. Goldschmidt, Essen
(3) BASF, Ludwigshafen
(4) Hüls, Troisdorf A G, Wiften
(5) Henkel, Düsseldorf
(6) H. B. Fuller GmbH, Lüneburg
(7) Goodrich, Neuss Sun Protection Lotion (W/O)

| | raw material | | % by weight |
|---|---|---|---|
| A | Monospher-conjugate | (1) | 5.00 |
| | Eusolex HMS | (1) | 5.00 |
| | Eusolex OS | (1) | 5.00 |
| | Eusolex OCR | (1) | 5.00 |
| | Abil WE 09 | (2) | 5.00 |
| | Jojoba oil | (3) | 3.00 |
| | Cetiol V | (4) | 3.00 |
| | Prisorine 2021 | (5) | 2.00 |
| | Lunacera M | (6) | 1.80 |
| | Miglyol 812 neutral oil | (7) | 3.00 |
| B | glycerine (about 87%) | (1) | 2.00 |
| | sodium chloride | (1) | 0.40 |
| | preservative | (1) | q.s. |
| | water, demineralized | | ad 100.00 |

Preparation

Phase B ist heated to 80° C. and phase A is heated to 75° C. Phase B is slowly introduced into phase A under stirring. The mixture ist homogenized and cooled while stirring.

Remarks
Preservative:
0.05% propyl-4-hydroxybenzoate 0.15% methyl-4-hydroxybenzoate Supply Sources (1) Merck KGaA, Darmstadt (2) Th. Goldschmidt A G, Essen (3) H. Lamotte, Bremen (4) Henkel KGaA, Düsseldorf (5) Unichema, Ermmerich (6) H. B. Fuller, Lüneburg (7) Hüls Troisdorf A G, Witten

| Sun protection cream (W/O) | | | |
|---|---|---|---|
| raw material | INCI | | % by weight |
| A Monospher-conjugate | | (1) | 2.50 |
| Eusolex T-2000 | micron. titanium dioxide | (1) | 2.50 |
| Eusolex 6300 | 4-methylbenzylidene camphor | (1) | 2.00 |
| Dehymuls E | dicocoyl pentaerythrityl citrate (and) sorbitan sesquioleate (and) cera alba (and) aluminum stearate | (2) | 6.00 |
| Arlacel 989 | PEG-7 hydrogenated castor oil | (3) | 1.00 |
| beeswax | cera alba | (1) | 2.00 |
| zinc stearate | zinc stearate | (1) | 2.00 |
| Cetiol J 600 | oleyl erucate | (2) | 6.00 |
| Cetiol V | decyl oleate | (2) | 6.00 |
| Cetiol OE | dicaprylyl ether | (2) | 5.00 |
| Dow Corning 200 (100 cs) | dimethicone | (4) | 1.00 |
| DL-α-tocopherolacetate | tocopheryl acetate | (1) | 1.00 |
| Vitamin A palmitate | retinyl palmitate | (5) | 0.50 |
| B Eusolex 232 | phenylbenzimidazole sulfonic acid | (1) | 2.00 |
| tris(hydroxymethyl)-aminomethane | tromethamine | (1) | 0.88 |
| glycerine (about 87%) | glycerine | (1) | 5.00 |
| magnesium sulfate heptahydrate | magnesium sulfate | (1) | 1.00 |
| allantoin | allantoin | (1) | 0.20 |
| preservative | | | q.s. |
| water, demineralized | | | ad 100.00 |

Preparation

In order to neutralize Eusolex 232 the tris (hydroxymethyl)-aminomethane is dissolved in the water of phase B and Eusolex 232 is added while stirring. After complete dissolution the residual raw materials of phase B are added and heated to 80° C. Phase A is heated to 75° C. Phase B is slowly added to phase A while stirring and the mixture is coated while stirring.

Remarks

Preservative:

0.05% propyl-4-hydroxybenzoate 0.15% methyl-4-hydroxybenzoate

Supply Sources (1) Merck KGaA, Darmstadt (2) Henkel KGaA, Duüsseldorf (3) ICI, Essen (4) Dow Corning, Düsseldorf (5) Hoffmann La Roche, Schweiz

| Sun protection gel (O/W) exhibiting UV-A/B screen | | | |
|---|---|---|---|
| | raw material | | % by weight |
| A | Monospher-conjugate | (1) | 2.00 |
| | Eusolex 2292 | (1) | 5.50 |
| | Oxynex K liquid | (1) | 1.00 |
| | Luvitol EHO | (2) | 9.00 |
| | Dow Corning 200 (100 cs) | (3) | 2.00 |
| | Antaron V-220 | (4) | 2.00 |
| | jojoba oil | (5) | 5.00 |
| B | tris(hydroxymethyl) aminomethane | (1) | 0.60 |
| | preservative | | q.s. |
| | water, demineralized | | ad 100.00 |
| C | Pemulen TR-1 | (6) | 0.50 |
| | water, demineralized | | 29.50 |
| D | Aloe Vera gel 1:10 | (7) | 1.00 |

Preparation

PemulenTR-1 is dispersed homogeneously in water and pre-swelled to obtain phase C. Phase B is introduced into phase C under homogenization. Phase A is dissolved by heating and added slowly under homogenization. Phase D is added at 35° C. and again homogenized.

Remarks

Preservative:

0.05% propyl-4-hydroxybenzoate 0.15% methyl-4-hydroxybenzoate

Supply Sources (1) E. Merck, Darmstadt (2) BASF, Ludwigshafen (3) Dow Corning, Düsseldorf (4) GAF, Frechen (5) Henry Lamotte, Bremen (6) Goodrich, Neuss (7) Galke, Gittelde

| Sun protection spray (O/W) | | | |
|---|---|---|---|
| raw material | INCI | | % by weight |
| A Monospher-conjugate | | (1) | 3.00 |
| Eusolex 2292 | octyl methoxycinnamate | (1) | 7.50 |
| Eusolex HMS | homosalate | (1) | 7.00 |
| Volpo S-2 | Steareth-2 | (2) | 0.40 |
| Volpo S-10 | Steareth-10 | (2) | 0.80 |
| Pemulen TR-2 | acrylate/$C_{10-30}$-alkyl acrylate crosspolymer | (3) | 0.18 |
| Hetester PHA | propylene glycol isoceteth-3 acetate | (4) | 500 |
| Performa V 825 | synthetic wax | (5) | 0.80 |
| Dow Corning 200 (100cs) | dimethicone | (6) | 1.00 |
| Oxynex K liquid | PEG-8 (and) tocopherol (and) ascorbyl palmitate (and) ascorbic acid (and) citric acid | (1) | 0.10 |
| B Eusolex 232 | phenylbenzimidazole sulfonic acid | (1) | 1.00 |
| triethanolamine | triethanolamine | (1) | 0.90 |
| propanediol-1,2 | propylene glycol | (1) | 2.00 |
| preservative | | | q.s. |
| water, demineralized | aqua | | ad 100.00 |

Preparation

In order to neutralize Eusolex 232 triethanolamine is added to the water of phase B and Eusolex 232 is added while stirring. After complete dissolution the residual raw materials of phase B are added and heated to 80° C. Phase A is s added with the exception of Pemulen and heated to 80° C. Then Pemulen is added to phase A while stirring. Phase B is slowly added to phase A while stirring and the mixture is homogenized and cooled while stirring.

Remarks

Preservative:

0.05% propyl-4-hydroxybenzoate 0.15% methyl-4-hydroxybenzoate

Supply Sources (1) Merck KGaf, Darmstadt (2) Croda, Nettetal (3) Goodrich, Neuss (4) ROVI, Schlüchtem (5) New Phase, NJ 08554

(6) Dow Corning, Wiesbaden

What is claimed is:

1. A conjugate, comprising an inorganic pigment and an active substance based on organic compounds being covalently bound through a spacer group to the inorganic pigment, characterized in that the spacer group contains an element of the groups 3A, 4A, 3B, 4B, 5B or 6B of the periodic table of elements.

2. The conjugate according to claim 1, wherein the inorganic pigment is a metal or semi-metal compound.

3. The conjugate according to claim 2, wherein the metal or semi-metal compound is an oxide, silicate, phosphate, carbonate, sulfate or nitride.

4. The conjugate according to claim 3, wherein the oxide is magnesium oxide, aluminum oxide, silicon oxide, zinc oxide, cerium oxide, titanium oxide, zirconium oxide, manganese oxide, boron oxide, iron oxide or a mixture of these oxides.

5. The conjugate according to claim 3, wherein the oxide is present in the form of spherical monodisperse oxide particles.

6. The conjugate according to claim 3, wherein the silicate is a mica or a talc.

7. The conjugate according to 1, comprising a particle size of from 1 nm to 250 μm.

8. The conjugate according to claim 1, wherein at least two molecules of the active substance are bound to a spacer group.

9. The conjugate according to claim 1, wherein the active substance is a compound selected from light absorbing organic compounds, substances having antioxidative and/or radical inhibiting properties, repellants, preservatives and derivatives of these active substances.

10. The conjugate according to claim 9, wherein the light absorbing organic compound is selected from derivatives of aminobenzoic acid, cinnamic acid, salicylic acid, benzylidene camphor, phenylbenzimidazole, diphenylacrylate, triazine, triazole, benzophenone, benzoylmethane, diarylbutadienes and vinyl group containing amides.

11. The conjugate according to claim 10, wherein the light absorbing organic compound is photostable.

12. The conjugate according to claim 9, wherein the substances having antioxidative and/or radical inhibiting properties are selected from flavonoides, coumaranones, vitamins and BHT.

13. The conjugate according to claim 9, wherein the repellants are selected from amides and derivatives thereof.

14. The conjugate according to claim 9, wherein the preservative are selected from benzoic acid and salt thereof, methylparaben, ethylparaben, propylparaben, sorbic acid and salts thereof and salicylic acid and salts thereof.

15. The conjugate according to claim 1, wherein the active substance is soluble in water and/or oil.

16. The conjugate according to claim 1, wherein the spacer group comprises a reactive metal center.

17. The conjugate according to claim 1, comprising the general formula (I)

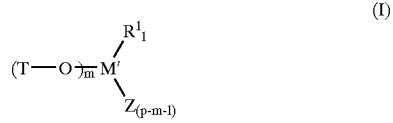

wherein:

T represents an oxide of an element, selected from the group Si, B, Al, Fe, Sn, Ti and Zr or a mixed oxide of these elements, being present in the core of the pigment;

M' represents a reactive metal center comprising an element of the groups 3A, 4A, 3B, 4B, 5B or 6B of the periodic table of elements;

$R^1$ represents the covalently bound reactive substance-group;

Z represents, identical or different, each H, OH, a halogen atom selected from F, Cl, Br, and/or an organic radical selected from A, OA, ACOO, $NA_2$, SA, saturated or unsaturated cycloalkyl having up to 6 carbon atoms, heterocyclic or aromatic radical Ar, wherein y is 0,1,2,3,4, A represents a straight, branched, saturated or unsaturated alkyl radical having from 1 to 8 carbon atoms and Ar represents substituted or unsubstituted phenyl, naphthyl, pyridyl, pyrimidinyl, thiophenyl, furanyl, wherein the substituents may be A, OA, COOH, COOA, Cl or F;

p represents the maximally possible valence of M';

m is 1, 2 or 3 and l is (p−m).

18. The conjugate according to claim 17, characterized in that $R^1$ is selected from the group consisting of

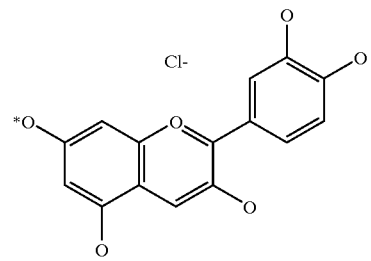

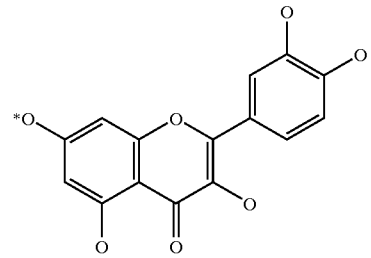

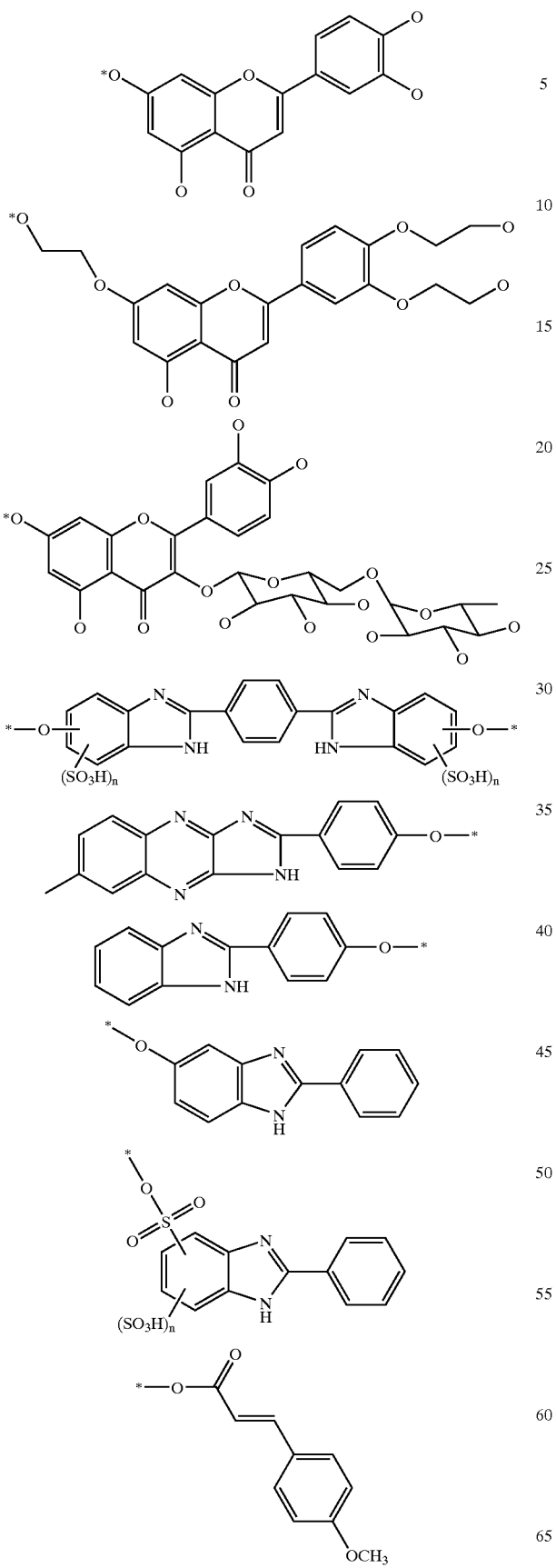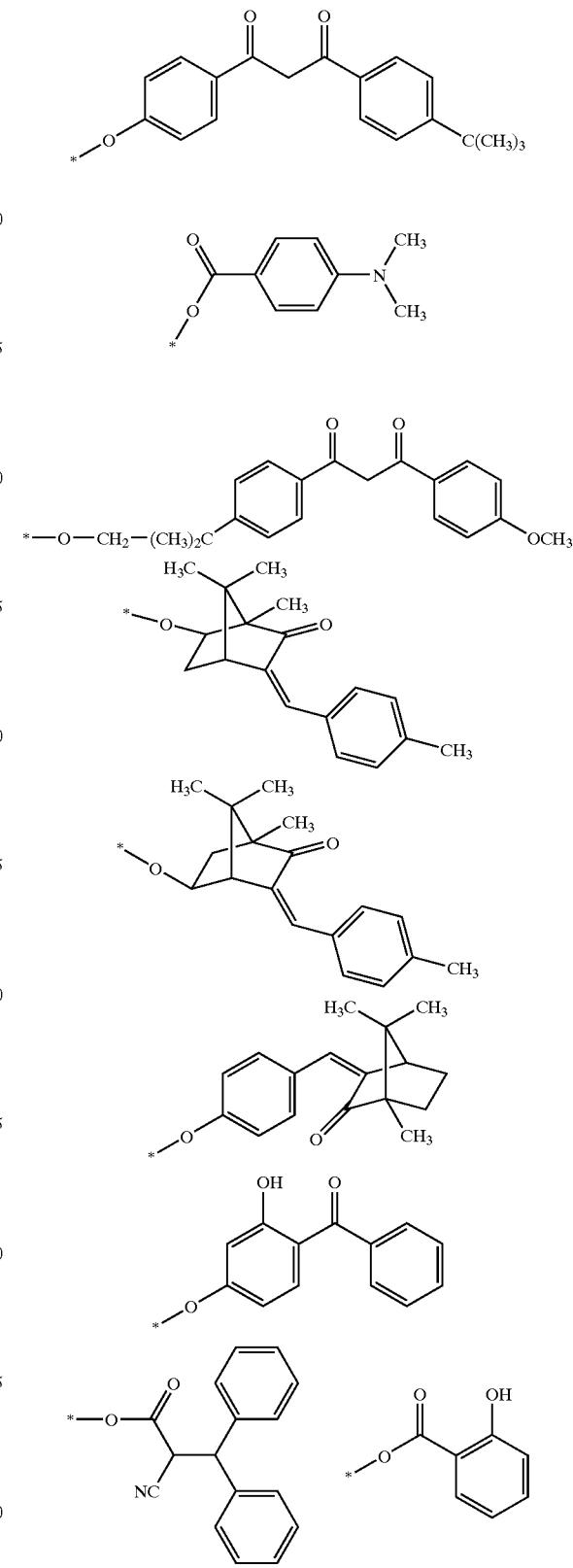
wherein n is 0, 1 or 2 and * represents the bond to the spacer-group.

19. A conjugate of the formula
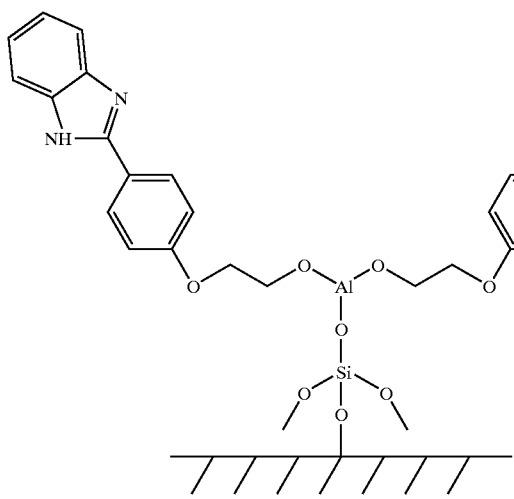
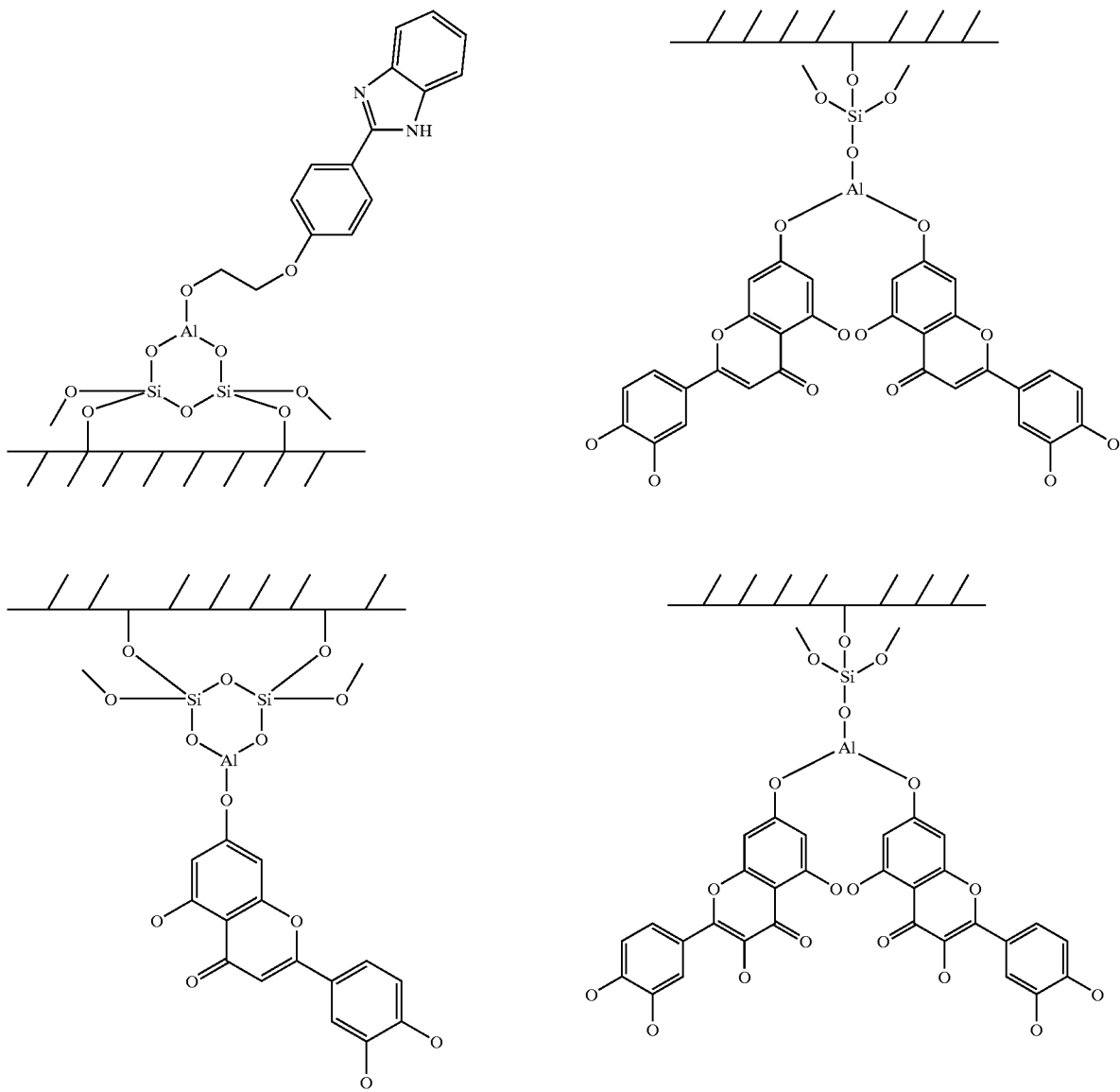

-continued
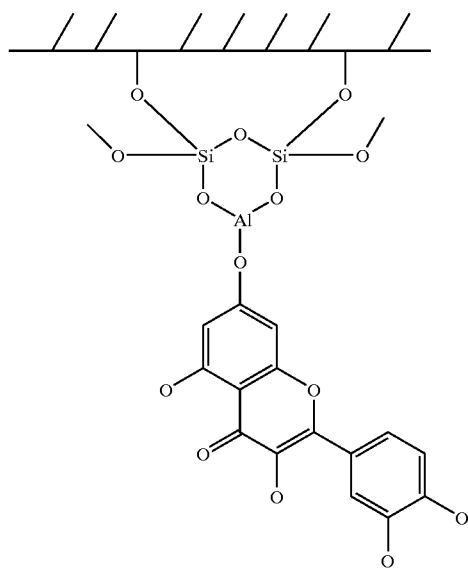
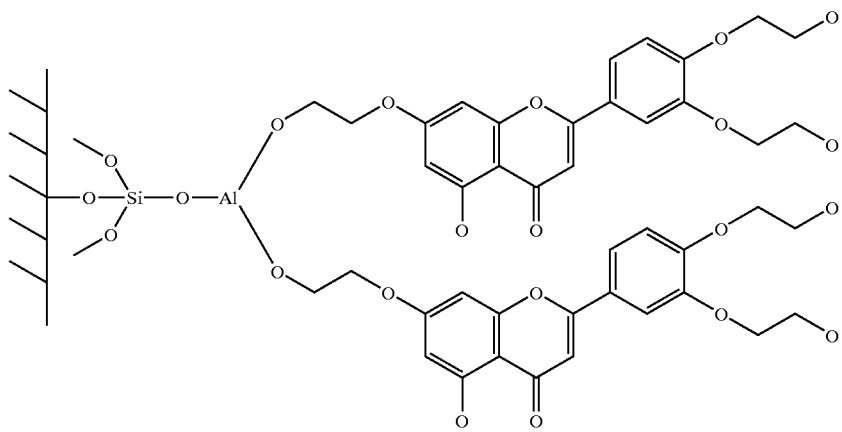
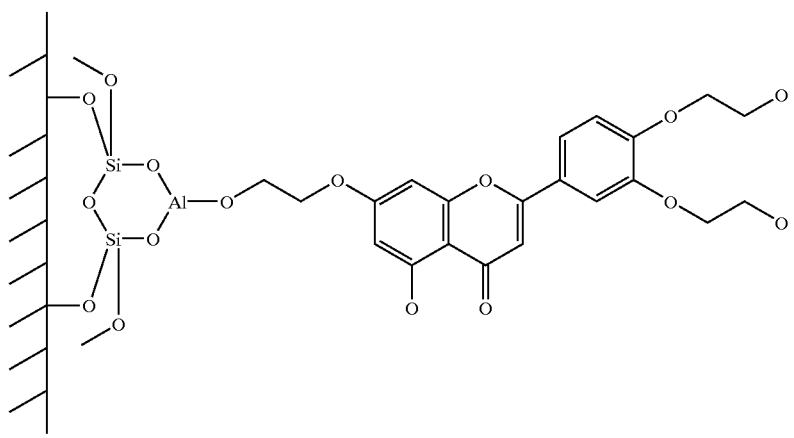

-continued
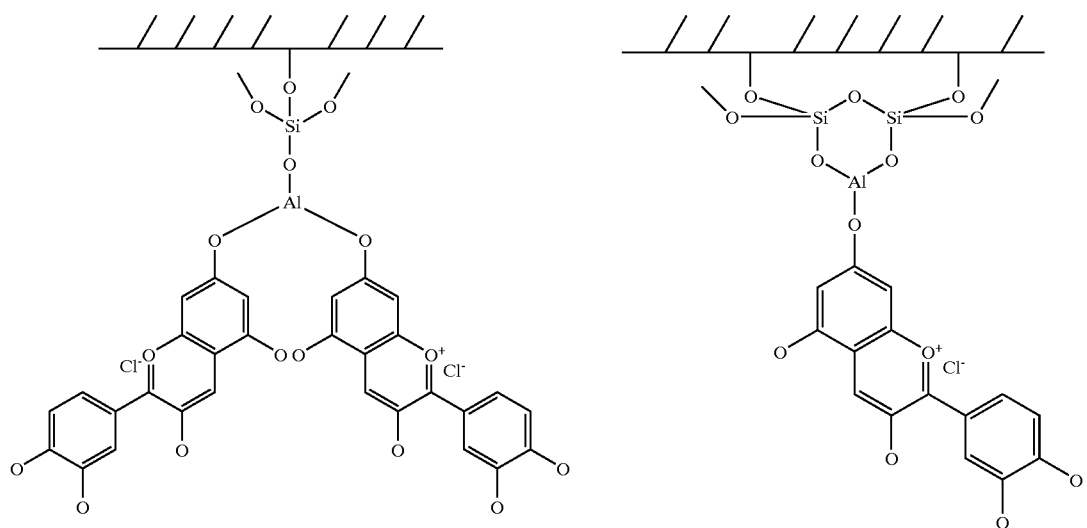
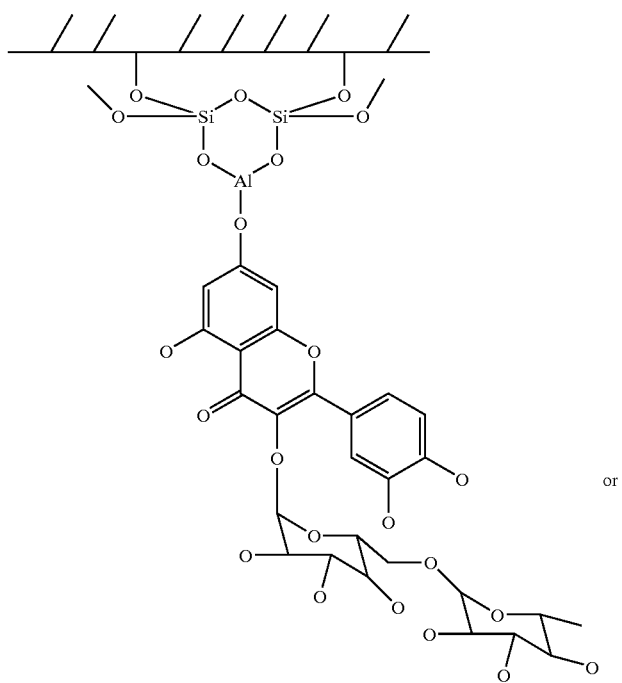
or

-continued

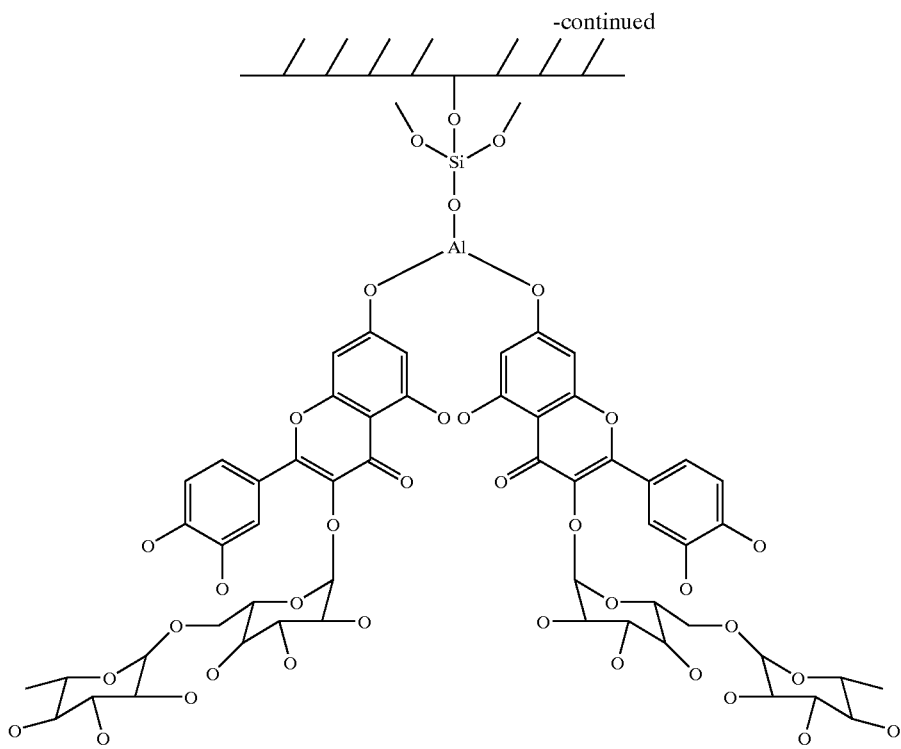

wherein the structures

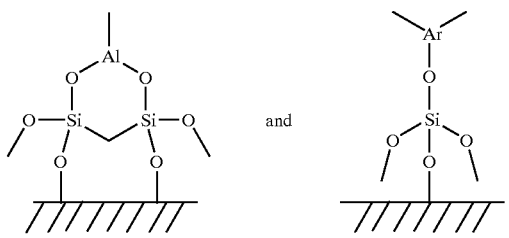

represent the inorganic support.

20. The conjugate according to claim 1, wherein the spacer group comprises an organic compound group.

21. The conjugate according to claim 20, wherein the organic compound group is represented by the formula —O(CH$_2$CH$_2$O)$_n$—, wherein n is an integer in the range of from 1 to 20.

22. The conjugate according to claim 21, wherein n is 1 or 2.

23. A dermatological or cosmetic composition comprising at least one conjugate according to claim 1, and at least one cosmetically, pharmaceutically and/or dermatologically compatible vehicle and/or adjuvant.

24. The dermatological composition according to claim 23, wherein it contains at least one further UV protecting substance.

25. The dermatological or cosmetic composition according to claim 23, wherein it contains an antioxidant.

26. A dispersion, comprising a conjugate according to claim 1, and an oil ingredient and/or a liquid light filter.

27. A process for preparing the conjugate according to claim 1, the process comprising:

(a) reacting a metal derivative, containing an element of the groups 3A, 4A, 3B, 4B, 5B or 6B of the periodic table of elements with an inorganic pigment to obtain a support material having a reactive surface, and (b) reacting the support material with an active substance based on organic substances and being capable of being coupled to bind the support material covalently to the active substance.

28. The process according to claim 27, wherein the support material having a reactive surface, before carrying out the step (b), is further reacted with an organic compound capable of being coupled in order to bind the support material covalently through an organic compound group to the active substance.

29. Use of the conjugate according to claim 1 for preparing a sun protection formulation or a skin protection formulation.

30. Use of the conjugate according to claim 1 for protecting skin cells.

31. The use according to claim 30 for protecting the Langerhans cells in the skin.

32. Use of the conjugate according to claim 1 for protecting the DNA.

33. Use of the conjugate according to claim 1 for immunoprotection.

* * * * *